(12) United States Patent
Dhawan et al.

(10) Patent No.: US 12,103,881 B2
(45) Date of Patent: *Oct. 1, 2024

(54) MOLECULES HAVING ONE HYDROPHOBIC GROUP AND TWO IDENTICAL HYDROPHILIC IONIC GROUPS AND COMPOSITIONS THEREOF AND METHODS OF PREPARATION THEREOF

(71) Applicant: ECOLAB USA INC., Saint Paul, MN (US)

(72) Inventors: Ashish Dhawan, Saint Paul, MN (US); Carter M. Silvernail, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/648,442

(22) Filed: Jan. 20, 2022

(65) Prior Publication Data

US 2022/0162102 A1    May 26, 2022

Related U.S. Application Data

(62) Division of application No. 16/116,222, filed on Aug. 29, 2018, now Pat. No. 11,261,113.

(Continued)

(51) Int. Cl.
*C02F 5/12* (2023.01)
*C07C 231/12* (2006.01)
(Continued)

(52) U.S. Cl.
CPC .............. *C02F 5/12* (2013.01); *C07C 231/12* (2013.01); *C07C 237/06* (2013.01);
(Continued)

(58) Field of Classification Search
CPC ........ C02F 1/1683; C02F 5/12; C02F 9/5407; C02F 2303/08; C02F 2305/04;
(Continued)

(56) References Cited

U.S. PATENT DOCUMENTS

| 2,195,974 A | 4/1940 | Reppe et al. |
| 3,077,487 A | 2/1963 | Ramsey et al. |

(Continued)

FOREIGN PATENT DOCUMENTS

| BE | 606234 A | 7/1961 |
| CA | 1084925 A | 9/1980 |

(Continued)

OTHER PUBLICATIONS

W. Y. Chen, B. Z. Xu, and X. D. Feng (S. T. Voong), Synthesis of Polysulfohexyl Methacrylate with Anticoagulant Activity, Journal of Polymer Science: Polymer Chemistry Edition, vol. 20,547-554 (1982) (Year: 1982).*

(Continued)

*Primary Examiner* — Bijan Ahvazi
(74) *Attorney, Agent, or Firm* — McKee, Voorhees & Sease, PLC

(57) ABSTRACT

A novel class of compounds is described here. The disclosed novel compounds have one hydrophilic group and two identical hydrophilic ionic groups. The two hydrophilic groups of the disclosed compounds contain or end with a cationic or anionic charged group. The disclosed novel compounds herein can be used as surfactants in an article, product, or composition, or for some other purposes. A method to synthesize the disclosed novel compounds is also described.

20 Claims, 2 Drawing Sheets

Related U.S. Application Data

(60) Provisional application No. 62/552,108, filed on Aug. 30, 2017.

(51) Int. Cl.

| | |
|---|---|
| *C07C 237/06* | (2006.01) |
| *C07F 9/54* | (2006.01) |
| *C11D 1/62* | (2006.01) |
| *C11D 3/386* | (2006.01) |
| *C11D 7/32* | (2006.01) |
| *C23F 11/10* | (2006.01) |
| *C23F 11/14* | (2006.01) |
| *C02F 1/68* | (2023.01) |

(52) U.S. Cl.
CPC .............. *C07F 9/5407* (2013.01); *C11D 1/62* (2013.01); *C11D 3/386* (2013.01); *C11D 7/3254* (2013.01); *C11D 7/3263* (2013.01); *C23F 11/10* (2013.01); *C23F 11/141* (2013.01); *C23F 11/149* (2013.01); *C02F 1/683* (2013.01); *C02F 2303/08* (2013.01); *C02F 2305/04* (2013.01)

(58) Field of Classification Search
CPC ......... C23F 11/10; C23F 11/14; C23F 11/149; C11D 1/62; C11D 3/386; C11D 7/3254; C11D 7/3263; C07C 231/12; C07C 237/06

See application file for complete search history.

(56) References Cited

U.S. PATENT DOCUMENTS

| | | |
|---|---|---|
| 4,075,136 A | 2/1978 | Schaper |
| 4,166,894 A | 9/1979 | Schaper |
| 4,195,138 A | 3/1980 | Ward |
| 4,246,030 A | 1/1981 | Lipinski |
| 4,259,217 A | 3/1981 | Murphy |
| 4,320,147 A | 3/1982 | Schaeufele |
| 4,355,071 A | 10/1982 | Chang |
| 4,705,665 A | 11/1987 | Malik |
| 4,798,675 A | 1/1989 | Lipinski et al. |
| 5,019,343 A | 5/1991 | Hwa et al. |
| 5,192,798 A | 3/1993 | Aiken et al. |
| 5,389,685 A | 2/1995 | Smith et al. |
| 5,399,746 A | 3/1995 | Steiger et al. |
| 5,545,749 A | 8/1996 | Smith et al. |
| 5,547,990 A | 8/1996 | Hall et al. |
| 5,614,616 A | 3/1997 | Buysch et al. |
| 5,738,795 A | 4/1998 | Chen |
| 5,833,741 A | 11/1998 | Walker |
| 6,004,466 A | 12/1999 | Derian et al. |
| 6,054,054 A | 4/2000 | Robertson et al. |
| 6,080,323 A | 6/2000 | Yu et al. |
| 6,090,754 A | 7/2000 | Chan et al. |
| 6,156,222 A | 12/2000 | Jennings et al. |
| 6,238,621 B1 | 5/2001 | Kalota et al. |
| 6,464,764 B1 | 10/2002 | Lichtenberg et al. |
| 6,503,880 B1 | 1/2003 | Skold et al. |
| 6,583,181 B1 | 6/2003 | Chiang et al. |
| 6,627,612 B1 | 9/2003 | O'Lenick, Jr. et al. |
| 6,797,785 B1 | 9/2004 | Hund et al. |
| 6,881,710 B1 | 4/2005 | O'Lenick, Jr. et al. |
| 6,939,840 B2 | 9/2005 | Lichtenberg et al. |
| 6,984,340 B1 | 1/2006 | Brady et al. |
| 7,052,614 B2 | 5/2006 | Barak |
| 7,084,129 B1 | 8/2006 | Smith et al. |
| 7,345,015 B1 | 3/2008 | Kong et al. |
| 7,375,064 B1 | 5/2008 | O'Lenick, Jr. |
| 7,507,399 B1 | 3/2009 | O'Lenick, Jr. |
| 7,604,978 B2 | 10/2009 | Eldridge |
| 8,221,733 B2 | 7/2012 | Lichtenberg et al. |
| 8,324,264 B1 | 12/2012 | Eldridge et al. |
| 8,933,055 B2 | 1/2015 | Pedersen et al. |
| 9,164,379 B2 | 10/2015 | Utsumi et al. |
| 9,956,153 B2 | 5/2018 | Emiru et al. |
| 10,206,392 B2 | 2/2019 | Kloeppel et al. |
| 10,285,400 B2 | 5/2019 | Lei et al. |
| 10,850,999 B2 | 12/2020 | DiMascio et al. |
| 10,945,431 B2 | 3/2021 | Karandikar et al. |
| 11,058,111 B2 | 7/2021 | Dhawan et al. |
| 11,084,974 B2 | 8/2021 | Dhawan et al. |
| 11,236,040 B2 | 2/2022 | Dhawan et al. |
| 11,261,113 B2 * | 3/2022 | Dhawan .................. C11D 1/62 |
| 11,292,734 B2 | 4/2022 | Dhawan et al. |
| 2001/0044393 A1 | 11/2001 | Peterson, Jr. et al. |
| 2002/0104349 A1 | 8/2002 | Richter et al. |
| 2002/0155978 A1 | 10/2002 | Man et al. |
| 2003/0029812 A1 | 2/2003 | Burns et al. |
| 2003/0114342 A1 | 6/2003 | Hall |
| 2003/0121532 A1 | 7/2003 | Coughlin et al. |
| 2003/0187073 A1 | 10/2003 | Lichtenberg et al. |
| 2004/0009139 A1 | 1/2004 | Oldenhove |
| 2004/0220275 A1 | 11/2004 | Lutzeler et al. |
| 2005/0061197 A1 | 3/2005 | Nalepa |
| 2005/0124723 A1 | 6/2005 | Fritschi et al. |
| 2005/0215461 A1 | 9/2005 | Gluck et al. |
| 2005/0261484 A1 | 11/2005 | Pascaly et al. |
| 2006/0008496 A1 | 1/2006 | Kulkarni et al. |
| 2006/0231505 A1 | 10/2006 | Mayer et al. |
| 2006/0289164 A1 | 12/2006 | Smith et al. |
| 2006/0289359 A1 | 12/2006 | Manek et al. |
| 2008/0152567 A1 | 6/2008 | Killough |
| 2009/0236571 A1 | 9/2009 | Cohen |
| 2010/0004316 A1 | 1/2010 | Lu et al. |
| 2010/0029530 A1 | 2/2010 | Whiteley |
| 2010/0305014 A1 | 12/2010 | Miralles et al. |
| 2011/0112007 A1 | 5/2011 | Hodge et al. |
| 2011/0296746 A1 | 12/2011 | Hernandez Altamirano et al. |
| 2012/0053111 A1 | 3/2012 | Hodge et al. |
| 2012/0070341 A1 | 3/2012 | Eder et al. |
| 2012/0071438 A1 | 3/2012 | Pedersen et al. |
| 2012/0115962 A1 | 5/2012 | Lee et al. |
| 2012/0258157 A1 | 10/2012 | Koltzenburg et al. |
| 2013/0266669 A1 | 10/2013 | Jiang et al. |
| 2013/0302736 A1 | 11/2013 | Utsumi et al. |
| 2014/0124454 A1 | 5/2014 | Nichols et al. |
| 2014/0171512 A1 | 6/2014 | Kloeppel et al. |
| 2014/0224733 A1 | 8/2014 | Osness et al. |
| 2015/0203738 A1 | 7/2015 | Witham et al. |
| 2015/0272124 A1 | 10/2015 | Pedersen et al. |
| 2015/0290100 A1 | 10/2015 | Eder et al. |
| 2016/0010035 A1 | 1/2016 | Liu et al. |
| 2016/0030315 A1 | 2/2016 | Emiru et al. |
| 2016/0130494 A1 | 5/2016 | Zaid et al. |
| 2016/0145610 A1 | 5/2016 | Lu et al. |
| 2016/0215198 A1 | 7/2016 | Qu et al. |
| 2016/0262999 A1 | 9/2016 | Pedersen et al. |
| 2016/0264734 A1 | 9/2016 | Boday et al. |
| 2016/0264744 A1 | 9/2016 | Boday et al. |
| 2017/0002145 A1 | 1/2017 | Boday et al. |
| 2017/0121560 A1 | 5/2017 | Dockery et al. |
| 2017/0130340 A1 | 5/2017 | Kalakodimi et al. |
| 2017/0233643 A1 | 8/2017 | Agashe et al. |
| 2017/0284605 A1 | 10/2017 | Janak et al. |
| 2017/0349543 A1 | 12/2017 | Siegwart et al. |
| 2017/0360040 A1 | 12/2017 | Kost et al. |
| 2018/0007895 A1 | 1/2018 | Karandikar et al. |
| 2018/0066211 A1 | 3/2018 | Pickering et al. |
| 2018/0105629 A1 | 4/2018 | Tada et al. |
| 2018/0118999 A1 | 5/2018 | Hikem et al. |
| 2018/0163020 A1 | 6/2018 | Zong et al. |
| 2018/0192643 A1 | 7/2018 | Fast et al. |
| 2019/0062187 A1 | 2/2019 | Dhawan et al. |
| 2019/0223434 A1 | 7/2019 | Balasubramanian et al. |
| 2019/0224627 A1 | 7/2019 | Glanz et al. |
| 2020/0071205 A1 * | 3/2020 | Dhawan .................. C08G 83/006 |
| 2020/0071261 A1 | 3/2020 | Dhawan et al. |
| 2020/0229435 A1 | 7/2020 | Malet et al. |
| 2020/0305437 A1 | 10/2020 | McGeechan et al. |

(56) References Cited

U.S. PATENT DOCUMENTS

| | | | |
|---|---|---|---|
| 2020/0332423 A1 | 10/2020 | Dhawan et al. | |
| 2022/0163891 A1 | 5/2022 | Eum et al. | |

FOREIGN PATENT DOCUMENTS

| | | | | |
|---|---|---|---|---|
| CA | 2357756 A1 | 7/2000 | | |
| CN | 1340031 A | 3/2002 | | |
| CN | 101972612 A | 2/2011 | | |
| CN | 102675535 A | 9/2012 | | |
| CN | 103118655 A | 5/2013 | | |
| CN | 103288672 A | 9/2013 | | |
| CN | 103483539 A | 1/2014 | | |
| CN | 104130335 A | 11/2014 | | |
| CN | 104130351 A | 11/2014 | | |
| CN | 104744709 A | 7/2015 | | |
| CN | 105076201 A | 11/2015 | | |
| CN | 105523956 A | 4/2016 | | |
| CN | 105884640 A | 8/2016 | | |
| CN | 106172434 A | 12/2016 | | |
| CN | 106423269 A | 2/2017 | | |
| CN | 106423284 A | 2/2017 | | |
| CN | 106634929 A | 5/2017 | | |
| CN | 106946743 A | 7/2017 | | |
| CN | 107440935 A | 12/2017 | | |
| CN | 108033895 A | 5/2018 | | |
| CN | 108048249 A | 5/2018 | | |
| CN | 108938662 A | 12/2018 | | |
| CN | 111315718 A | 6/2020 | | |
| DE | 1149363 B | 5/1963 | | |
| EP | 0185970 A1 | 7/1986 | | |
| EP | 0296441 A2 | 12/1988 | | |
| EP | 0327379 A2 | 8/1989 | | |
| EP | 0900266 B1 | 10/2002 | | |
| EP | 1690960 A2 | 8/2006 | | |
| EP | 2333135 A1 | 6/2011 | | |
| GB | 847321 | 9/1960 | | |
| GB | 941752 | 11/1963 | | |
| GB | 1550420 | * | 8/1979 | |
| GB | 1550420 A | 8/1979 | | |
| JP | S44031461 B | 12/1969 | | |
| JP | 57185322 A | 11/1982 | | |
| JP | S58105908 A | 6/1983 | | |
| JP | S6139937 B2 | 9/1986 | | |
| JP | 6259602 A | 3/1987 | | |
| JP | 0291590 A1 | * | 11/1988 | ............. C04B 24/16 |
| JP | 913066 A | 1/1997 | | |
| JP | 2001187751 A | 7/2001 | | |
| JP | 200777082 A | 3/2007 | | |
| JP | 2007054710 A | 3/2007 | | |
| JP | 2007256445 A | 10/2007 | | |
| JP | 2012136504 A | 7/2012 | | |
| JP | 2014009177 A | 1/2014 | | |
| JP | 2014093768 A | 5/2014 | | |
| JP | 2014221859 A | 11/2014 | | |
| JP | 2015101552 A | 6/2015 | | |
| JP | 2015189857 A | 11/2015 | | |
| JP | 2017525798 A | 9/2017 | | |
| WO | 0035283 A1 | 6/2000 | | |
| WO | 0039241 A1 | 7/2000 | | |
| WO | 0059696 A2 | 10/2000 | | |
| WO | 03035797 A1 | 5/2003 | | |
| WO | 2004046211 A1 | 6/2004 | | |
| WO | 2004056843 A2 | 7/2004 | | |
| WO | WO-2006092736 A2 | * | 9/2006 | .......... B01F 17/0042 |
| WO | 2008049616 A1 | 5/2008 | | |
| WO | 2008079729 A1 | 7/2008 | | |
| WO | 2009153209 A1 | 12/2009 | | |
| WO | 2012083497 A1 | 6/2012 | | |
| WO | 2013087287 A1 | 6/2013 | | |
| WO | 2014079621 A1 | 5/2014 | | |
| WO | 2015084304 A1 | 6/2015 | | |
| WO | 2016205513 A1 | 12/2016 | | |
| WO | 2017003639 A2 | 1/2017 | | |
| WO | 2017184113 A1 | 10/2017 | | |
| WO | 2017201076 A1 | 11/2017 | | |
| WO | 2018112548 A1 | 6/2018 | | |
| WO | 2019046409 A1 | 3/2019 | | |

OTHER PUBLICATIONS

Bosica et al., "Aza-Michael Mono-addition Using Acidic Alumina under Solventless Conditions", Molecules, vol. 21, 11 pages, Jun. 22, 2016.

Mann et al., "Acetal initiated cyclization of allylsilanes to highly functionalized piperidine derivatives", Tetraedron Letters, vol. 29(26), pp. 3247-3250, 1988.

Registry 790647-93-7, accessed online on Aug. 14, 2021, 1 page, registered Nov. 30, 2004.

Registry 881538-24-5, accessed online on Aug. 14, 2021, 1 page, registered Apr. 21, 2006.

Registry 881538-25-6, accessed online on Aug. 14, 2021, 1 page, registered Apr. 21, 2006.

Registry 881538-26-7, accessed online on Aug. 14, 2021, 1 page, registered Apr. 21, 2006.

Registry 930395-29-2, accessed online on Aug. 14, 2021, 1 page, registered Apr. 17, 2007.

Registry 951236-20-7, accessed online on Aug. 14, 2021, 1 page, registered Oct. 23, 2007.

Registry 951236-22-9, accessed online on Aug. 14, 2021, 1 page, registered Oct. 23, 2007.

Registry 951236-51-4, accessed online on Aug. 14, 2021, 1 page, registered Oct. 23, 2007.

Registry 1025555-14-9, accessed online on Aug. 14, 2021, 1 page, registered Jun. 5, 2008.

Registry 1025555-15-0, accessed online on Aug. 14, 2021, 1 page, registered Jun. 5, 2008.

Registry 1346596-75-5, accessed online on Aug. 14, 2021, 1 page, registered Nov. 30, 2011.

Registry 1346596-76-6, accessed online on Aug. 14, 2021, 1 page, registered Nov. 30, 2011.

Registry 1346596-77-7, accessed online on Aug. 14, 2021, 1 page, registered Nov. 30, 2011.

Registry 1801234-01-4, accessed online on Aug. 14, 2021, 1 page, registered Aug. 3, 2015.

Registry 1801234-02-5, accessed online on Aug. 14, 2021, 1 page, registered Aug. 3, 2015.

Registry 2000293-27-4, accessed online on Aug. 14, 2021, 1 page, registered Sep. 26, 2016.

Registry 2001056-21-7, accessed online on Aug. 14, 2021, 1 page, registered Sep. 27, 2016.

Twyman, Lance J., "Post synthetic modification of the hydrophobic interior of a water-soluble dendrimer", Tetrahedron Letters, vol. 41(35), pp. 6875-6878, 2000.

Zielinksi, Wojciech et al., "TI-Synthesis of new quaternary ammonium salts for organophilization of fillers for polymeric nanocomposites", D1: Database Chemical Abstracts [Online] chemical abstracts; XP55789968, Database accession No. 2007:1236240 Jan. 1, 2007.

European Patent Office, "Extended European Search Report", issued in connection to Application No. 18850998.8, 3 pages, mailed Apr. 7, 2021.

Labade et al., "Cesium fluoride catalyzed Aza-Michael addition reaction in aqueous media" Montash Chem., vol. 142, pp. 1055-1059, published Jul. 19, 2011.

Zhang et al., "Controllable Self-Assembly of Amphiphilic Dendrimers on a Silica Surface: The Effect of Molecular Topological Structure and Salinity", Journal of Physical Chemistry, vol. 8, pp. 10990-10999, Oct. 5, 2016.

Zhang et al., "Supporting Information", Beijing National Laboratory for Molecular Sciences, published with "Controllable Self-Assembly of Amphiphilic Dendrimers on a Silica Surface: Effect of Molecular Topological Structure and Salinity", 4 pages Oct. 5, 2016.

Somerscales, Euan F.C., "Fundamentals of Corrosion Fouling", Experimental Thermal and Fluid Science, vol. 14, pp. 335-355, 1997.

(56) References Cited

OTHER PUBLICATIONS

Ecolab USA Inc., in connection with PCT/US2019/048441 filed Aug. 28, 2019, "Written Opinion of International Preliminary Examining Authority" 7 pages, mailed Jul. 15, 2020.
Zielinski et al., "Synteza nowych czwartorzedowych soli amoniowych do organofilizacji nanokompozytowych hapelniaczy polimerowych", www.miesiecznikchemik.pl, 2007.
Bosica et al., "Aza-Michael Mono-addition Using Acidic Alumina under Solventless Conditions", Molecules, vol. 21, No. 6, doi: 10.3390/molecules21060815, p. 815, 2016.
Zhou et al., "Cooperative binding and self-assembling behavior of cationic low molecular-weight dendrons with RNA molecules", Organic & Biomolecular Chemistry, vol. 4, pp. 581-585, 2006.
Ecolab USA Inc, in connection with PCT/US2018/048518 filed Aug. 29, 2018, "The International Search Report and the Written Opinion of the International Searching Authority, or the Declaration", 10 pages, mailed Nov. 7, 2018.
Fan et al., "Synthesis and Aggregation Behavior of a Hexameric Quaternary Ammonium Surfactant", Langmuir, vol. 27, pp. 10570-10579, Jul. 28, 2011.
Zhang et al., "PAMAM-Based Dendrimers with Different Alkyl Chains Self-Assemble on Silica Surfaces: Controllable Layer Structure and Molecular Aggregation", J. Phys. Chem. B, vol. 122, pp. 6648-6655, Jun. 13, 2018.
Brycki et al., "The biodegradation of monomeric and dimeric alkylammonium surfactants", Journal of Hazardous Materials, vol. 280, pp. 797-815, Aug. 6, 2014.
Gan et al., "Sugar-Based Ester Quaternary Ammonium Compounds and Their Surfactant Properties", Journal of Surfactants and Detergents, vol. 17, Issue 3, pp. 465-470, Jan. 18, 2014.
Negm et al., "Synthesis, Characterization and Biological Activity of Sugar-Based Gemini Cationic Amphiphiles", Journal of Surfactants and Detergents, vol. 11, Issue 3, pp. 215-221, Jun. 13, 2008.
Tan et al., "The use of quaternised chitosan-loaded PMMA to inhibit biofilm formation and downregulate the virulence-associated gene expression of antibiotic-resistant *Staphylococcus*", Biomaterials, vol. 33, Issue 2, pp. 365-377, Jan. 2012.
Zaky, Mohamad, "Biocidal Activities of Cationic Surface Active Starch and Its Transition Metal Complexes Against Different Bacterial Strains", Journal of Surfactants and Detergents, vol. 13, Issue 3, pp. 255-260, Jul. 2010.
Zhi et al., "Self-aggregation and antimicrobial activity of saccharide-cationic surfactants", Colloids and Surfaces A: Physicochemical and Engineering Aspects, vol. 456, pp. 231-237, Aug. 2014.
"Azamethonium", http://pubchem.ncbi.nlm.nih.gov/compound/9383, last modified Oct. 6, 2018 and accessed by Applicant Oct. 11, 2018.
Kawakami et al., "Antibacterial Activity of Radial Compounds with Peripheral Quaternary Ammonium Units", Transactions of the Materials Research Society of Japan, vol. 35[4], pp. 885-887, 2010.
Miller et al., "Non-viral CRISPR/Cas gene editing in vitro and in vivo enabled by synthetic nanoparticle co-delivery of Cas9 mRNA and sgRNA", Angew Chem Int Ed Engl., 56(4), pp. 1059-1063, Jan. 19, 2018.
Ning et al., "Synthesis and characterization of a novel non-polyether demulsifier", http://en.cnki.com.cn/Artcle_en/CJFDTOTAL-HXGC201301020.htm, accessed online on Aug. 28, 2018, published 2013.
Wang et al., "A novel environment-sensitive biodegradable polydisulfide with protonatable pendants for nucleic acid delivery", Journal of Controlled Release, vol. 120, pp. 250-258, May 21, 2007.

\* cited by examiner

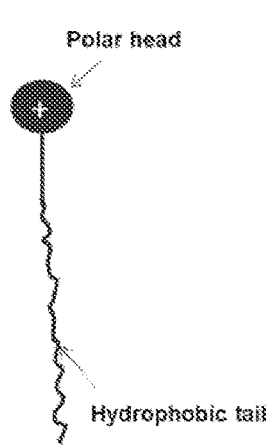
FIG. 1A Conventional Surfactants
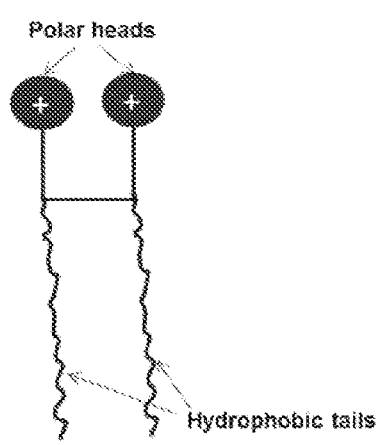
FIG. 1B Gemini (dicationic) Surfactants
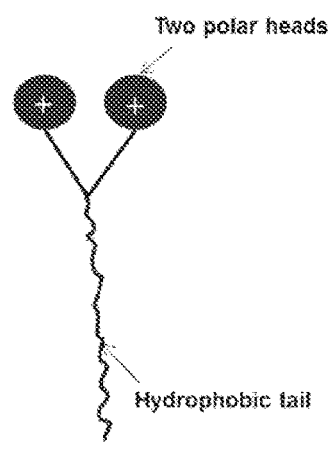
FIG. 1C Claimed Dicationic Surfactants

MOLECULES HAVING ONE HYDROPHOBIC GROUP AND TWO IDENTICAL HYDROPHILIC IONIC GROUPS AND COMPOSITIONS THEREOF AND METHODS OF PREPARATION THEREOF

CROSS-REFERENCE TO RELATED APPLICATIONS

This is a divisional application of U.S. Ser. No. 16/116,222, filed on Aug. 29, 2018, which claims priority and is related to U.S. Provisional Application Ser. No. 62/552,108, filed on Aug. 30, 2017, and entitled "MOLECULES HAVING ONE HYDROPHOBIC AND TWO IDENTICAL HYDROPHILIC GROUPS AND COMPOSITIONS THEREOF AND METHODS OF PREPARATION THEREOF." The entire contents of this patent application are hereby expressly incorporated herein by reference including, without limitation, the specification, claims, and abstract, as well as any figures, tables, or drawings thereof.

FIELD OF THE INVENTION

The present disclosure relates generally to the field of surfactant compounds and methods of making the same. In particular, the present disclosure is related to a new class of compounds that comprise two identical hydrophilic cationic or anionic groups and one hydrophobic group. The disclosed compounds share some structural features with conventional or Gemini surfactants but are structurally distinguishable from existing surfactants. The disclosed compounds are useful as a surfactant alone or together with other conventional or Gemini surfactant(s) in various applications.

BACKGROUND OF THE INVENTION

A surfactant compound usually contains a hydrophilic group and hydrophobic group. Because of its unique structure, a surfactant has various applications in different fields. As the understanding of the relationship between a surfactant compound's structure and its function and mode of operation improves, the need for surfactant compounds having new or improved properties, such as surface tension properties, is increasing.

Although structures of surfactants are diverse and numerous, the existing surfactants can be classified into two broad categories; one of conventional surfactants and another of Gemini surfactants.

A conventional surfactant usually has a hydrophobic group and a hydrophilic group. Depending on the characteristics of the hydrophilic group, a conventional surfactant can be one of nonionic, anionic, cationic, amphoteric, or zwitterionic surfactants.

A Gemini surfactant, on the other hand, has two hydrophobic groups and two hydrophilic groups. Gemini surfactants can be further divided similar subcategories based on the characteristics of the hydrophobic group(s), in an analogous manner as used for classifying a conventional surfactant.

Accordingly, it is an objective to develop novel surfactant compounds having properties distinguishable from conventional and/or Gemini surfactants. In both conventional and Gemini surfactants, the ratio of hydrophilic group to hydrophobic group is 1:1, while the disclosed compounds have a ratio of hydrophilic group to hydrophobic group of 2:1. This difference in the ratio of hydrophilic group to hydrophobic group provides for unique applications of the disclosed compounds, not only as surfactants, but also as antimicrobials, sanitizers, fabric softeners, antistatic agents, corrosion inhibitors, foaming agents, floatation collectors, dispersants, surfactants assisted enhanced oil recovery (EOR), cleaners, etc.

It is a further objective of the disclosure to develop a method to make the novel compounds efficiently and effectively.

It is a further objective of the disclosure to use the novel compounds in an article, product, and/or composition.

These and other objects, advantages and features of the present disclosure will become apparent from the following specification taken in conjunction with the claims set forth herein.

BRIEF SUMMARY OF THE INVENTION

Disclosed herein are novel compounds, including surfactant compounds, compositions comprising the disclosed compounds and methods of making the disclosed compounds. More particularly, disclosed herein are the compounds comprising two identical hydrophilic groups and a single hydrophobic group. In a disclosed compound, each hydrophilic group includes or ends in a quaternary amine or a negatively charged species, and the hydrophobic group includes a long hydrophobic chain. The disclosed compounds are different from conventional or Gemini surfactants, because the ratio of hydrophilic groups to hydrophobic group in the closed compounds is 2:1, while in conventional or Gemini surfactants the ratio is 1:1. This difference in structure provides unique applications for the disclosed compounds, not only as surfactants, but also for other purposes, such as antimicrobial sanitizers, fabric softeners, antistatic agents, corrosion inhibitors, foaming agents, floatation collectors, dispersants, surfactants assisted enhanced oil recovery (EOR), cleaners, etc.

In one aspect, a compound according to Formula I is provided:

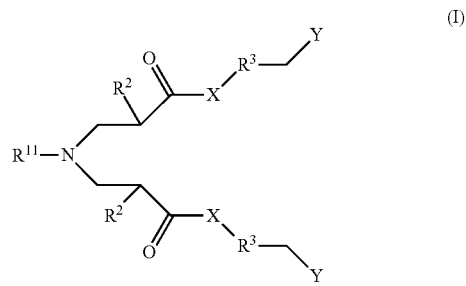

(I)

wherein
X is NH, or O;
$R^{11}$ is $R^1$ or $R^1$—Z—$(CH_2)_m$—;
$R^1$ is an unsubstituted or substituted, linear or branched $C_1$-$C_{30}$ alkyl, cyclic alkyl, alkenyl, or alkynyl group;
Z is NH or O;
$R^2$ is H, $CH_3$, or an unsubstituted, linear or branched $C_1$-$C_{10}$ alkyl, alkenyl, or alkynyl group;
m is an integer of 1 to 4;
$R^3$ is absent or an unsubstituted, linear $C_1$-$C_{30}$ alkylene group;
Y is —$NR_4R_5R_6^{(+)}$ or a salt thereof; and
$R^4$, $R^5$, and $R^6$ are independently $C_1$-$C_{10}$ alkyl group.

In other aspect, disclosed herein is a method to synthesize the disclosed compounds. The method comprises contacting a primary amine with an activated olefin containing at least one cationic group to generate any compound disclosed herein; wherein the primary amine is $R^{11}$—$NH_2$, $R^{11}$ is $R^1$ or $R^1$—Z—$(CH_2)_m$—; the activated olefin is

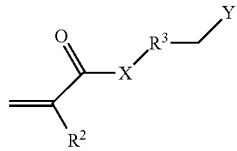

X is NH, or O;
$R^{11}$ is $R^1$ or $R^1$—Z—$(CH_2)_m$—;
$R^1$ is an unsubstituted or substituted, linear or branched $C_1$-$C_{30}$ alkyl, cyclic alkyl, alkenyl, or alkynyl group;
Z is NH or O;
$R^2$ is H, $CH_3$, or an unsubstituted, linear or branched $C_2$-$C_{10}$ alkyl, alkenyl, or alkynyl group;
m is an integer of 1 to 4;
$R^3$ is absent or an unsubstituted, linear $C_1$-$C_{30}$ alkylene group;
Y is —$NR_4R_5R_6^{(+)}$ or a salt thereof; and
$R^4$, $R^5$, and $R^6$ are independently $C_1$-$C_{10}$ alkyl group.

In yet another aspect, provided herein is an article, product, or composition that comprises one or more compounds disclosed herein.

In yet another aspect, provided herein is a composition comprising one or more compounds disclosed herein.

The forgoing summary is illustrative only and is not intended to be in any way limiting. In addition to the illustrative aspects, embodiments and features described above, further aspects, embodiments, and features of the present technology will become apparent to those skilled in the art from the following drawings and the detailed description, which shows and describes illustrative embodiments of the present technology. Accordingly, the figures and detailed description are also to be regarded as illustrative in nature and not in any way limiting.

BRIEF DESCRIPTION OF DRAWINGS

FIG. 1A shows a comparative representation of a conventional surfactant.

FIG. 1B shows a comparative representation of a Gemini surfactant.

FIG. 1C shows a representation of an exemplary compound of the disclosure.

Figure 2:
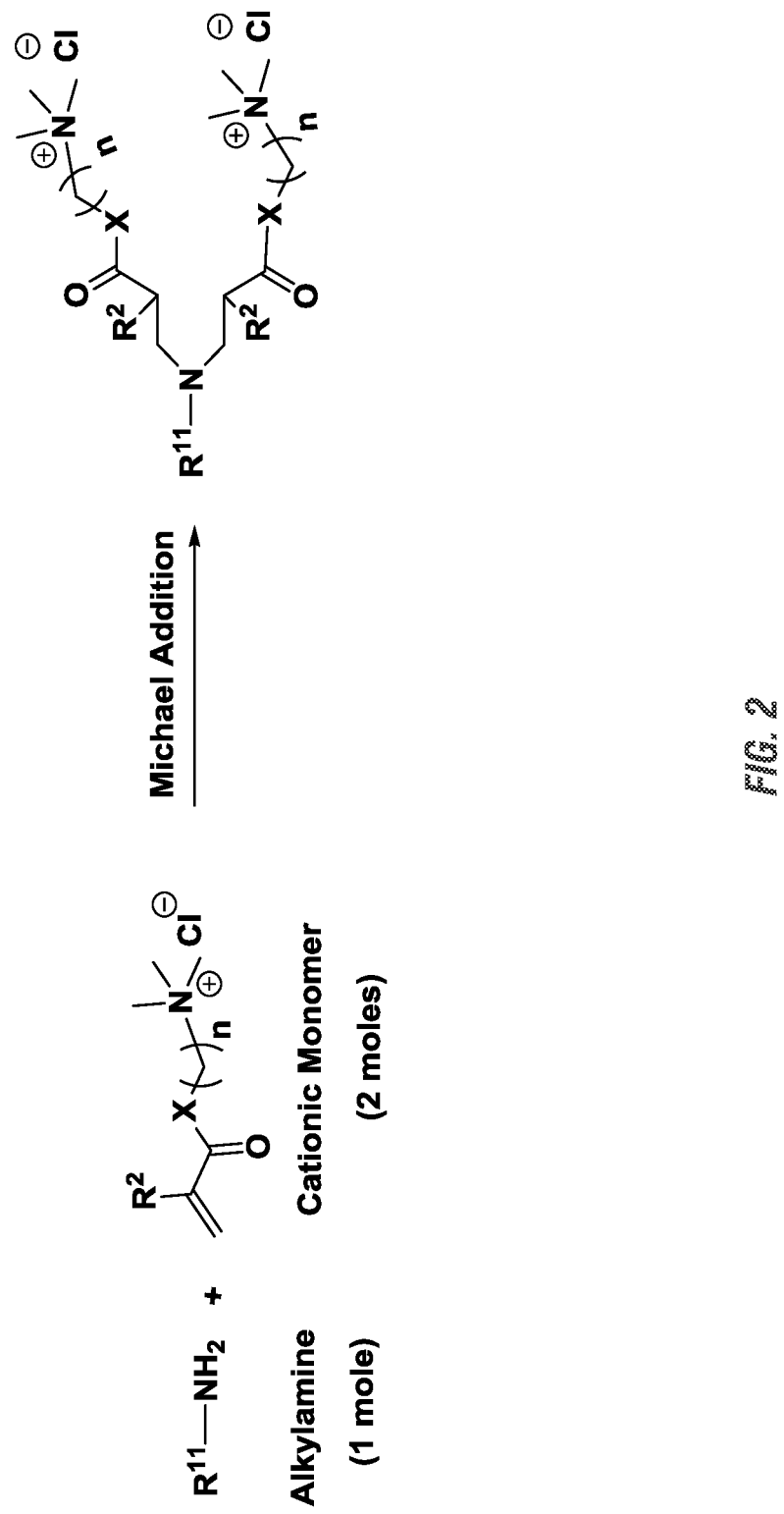
FIG. 2 shows a generic reaction scheme between a primary amine (Michael donor) and activated olefin (Michael acceptor) including a cationic group (Michael acceptor).

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

Disclosed herein are novel compounds and methods of making these novel compounds or surfactant compositions. More particularly, compounds comprising two identical hydrophilic groups and one hydrophobic group in the molecule, and methods of synthesizing such surfactants are disclosed. For example, each hydrophilic group includes or ends with a quaternary amine and the hydrophobic group includes a long aliphatic chain.

The embodiments of this invention are not limited to particular compositions and methods of use which can vary and are understood by skilled artisans. It is further to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. The description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through error in these procedures; through differences in the manufacture, source, or purity of the ingredients used to make the compositions or carry out the methods; and the like. The term "about" also encompasses amounts that differ due to novel equilibrium conditions for a composition resulting from a particular initial mixture. Whether or not modified by the term "about", the claims include equivalents to the quantities.

As used herein, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to carbon(s) or hydrogen(s) atom replaced by one or more bonds, including double or triple bonds, to a heteroatom. Thus, a substituted group is substituted with one or more substituents, unless otherwise specified. A substituted group can be substituted with 1, 2, 3, 4, 5, or 6 substituents.

Substituted ring groups include rings and ring systems in which a bond to a hydrogen atom is replaced with a bond to a carbon atom. Therefore, substituted cycloalkyl, aryl, heterocyclyl, and heteroaryl groups may also be substituted with substituted or unsubstituted alkyl, alkenyl, and alkynyl groups are defined herein.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Alkenyl groups or alkenes are straight chain, branched, or cyclic alkyl groups having two to about 30 carbon atoms, and further including at least one double bond. In some embodiments, an alkenyl group has from 2 to about 30 carbon atoms, or typically, from 2 to 10 carbon atoms. Alkenyl groups may be substituted or unsubstituted. For a double bond in an alkenyl group, the configuration for the double bond can be a trans or cis configuration. Alkenyl groups may be substituted similarly to alkyl groups.

Alkynyl groups are straight chain, branched, or cyclic alkyl groups having two to about 30 carbon atoms, and further including at least one triple bond. In some embodiments, an alkynyl group has from 2 to about 30 carbon atoms, or typically, from 2 to 10 carbon atoms. Alkynyl groups may be substituted or unsubstituted. Alkynyl groups may be substituted similarly to alkyl or alkenyl groups.

As used herein, the terms "alkylene", "cycloalkylene", "alkynylides", and "alkenylene", alone or as part of another substituent, refer to a divalent radical derived from an alkyl, cycloalkyl, or alkenyl group, respectively, as exemplified by —$CH_2CH_2CH_2$—. For alkylene, cycloalkylene, alkynylene, and alkenylene groups, no orientation of the linking group is implied.

The term "ester" as used herein refers to —$R^{30}COOR^{31}$ group. $R^{30}$ is absent, a substituted or unsubstituted alkylene, cycloalkylene, alkenylene, alkynylene, arylene, aralkylene, heterocyclylalkylene, or heterocyclylene group as defined herein. $R^{31}$ is a substituted or unsubstituted alkyl, cycloalkyl, alkenyl, alkynyl, aryl, aralkyl, heterocyclylalkyl, or heterocyclyl group as defined herein.

The term "amine" (or "amino") as used herein refers to —$R^{32}NR^{33}R^{34}$ groups. $R^{32}$ is absent, a substituted or unsubstituted alkylene, cycloalkylene, alkenylene, alkynylene, arylene, aralkylene, heterocyclylalkylene, or heterocyclylene group as defined herein. $R^{33}$ and $R^{34}$ are independently hydrogen, or a substituted or unsubstituted alkyl, cycloalkyl, alkenyl, alkynyl, aryl, aralkyl, heterocyclylalkyl, or heterocyclyl group as defined herein.

The term "amine" as used herein also refers to an independent compound. When an amine is a compound, it can be represented by a formula of $R^{32'}NR^{33'}R^{34'}$ groups, wherein $R^{32'}$, $R^{33'}$, and $R^{34'}$ are independently hydrogen, or a substituted or unsubstituted alkyl, cycloalkyl, alkenyl, alkynyl, aryl, aralkyl, heterocyclylalkyl, or heterocyclyl group as defined herein.

The term "alcohol" as used herein refers to —$R^{35}OH$ groups. $R^{35}$ is absent, a substituted or unsubstituted alkylene, cycloalkylene, alkenylene, alkynylene, arylene, aralkylene, heterocyclylalkylene, or heterocyclylene group as defined herein.

The term "carboxylic acid" as used herein refers to —$R^{36}COOH$ groups. $R^{36}$ is absent, a substituted or unsubstituted alkylene, cycloalkylene, alkenylene, alkynylene, arylene, aralkylene, heterocyclylalkylene, or heterocyclylene group as defined herein.

The term "ether" as used herein refers to —$R^{37}OR^{38}$ groups. $R^{37}$ is absent, a substituted or unsubstituted alkylene, cycloalkylene, alkenylene, alkynylene, arylene, aralkylene, heterocyclylalkylene, or heterocyclylene group as defined herein. $R^{38}$ is a substituted or unsubstituted alkyl, cycloalkyl, alkenyl, alkynyl, aryl, aralkyl, heterocyclylalkyl, or heterocyclyl group as defined herein.

The term "solvent" as used herein refers to any inorganic or organic solvent. Solvents are useful in the disclosed method or article, product, or composition as reaction solvent or carrier solvent. Suitable solvents include, but are not limited to, oxygenated solvents such as lower alkanols, lower alkyl ethers, glycols, aryl glycol ethers and lower alkyl glycol ethers. Examples of other solvents include, but are not limited to, methanol, ethanol, propanol, isopropanol and butanol, isobutanol, ethylene glycol, diethylene glycol, triethylene glycol, propylene glycol, dipropylene glycol, hexylene glycol, mixed ethylene-propylene glycol ethers, ethylene glycol phenyl ether, and propylene glycol phenyl ether. Water is a solvent too. The solvent used herein can be of a single solvent or a mixture of many different solvents.

Glycol ethers include, but are not limited to, diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether, propylene glycol phenyl ether, and the like, or mixtures thereof.

In one aspect, disclosed herein is a compound according to Formula I

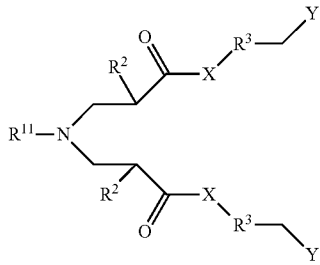

(I)

wherein
X is NH, or O;
R$^{11}$ is R$^1$ or R$^1$—Z—(CH$_2$)$_m$—;
R$^1$ is an unsubstituted or substituted, linear or branched C$_1$-C$_{30}$ alkyl, cyclic alkyl, alkenyl, or alkynyl group;
Z is NH or O;
R$^2$ is H, CH$_3$, or an unsubstituted, linear or branched C$_2$-C$_{10}$ alkyl, alkenyl, or alkynyl group;
m is an integer of 1 to 4;
R$^3$ is absent or an unsubstituted, linear C$_1$-C$_{30}$ alkylene group;
Y is —NR$_4$R$_5$R$_6$$^{(+)}$ or a salt thereof; and
R$^4$, R$^5$, and R$^6$ are independently C$_1$-C$_{10}$ alkyl group.

In some embodiments of the disclosed compounds herein, X is NH. In some other embodiments, X is O.

In some embodiments, R$^{11}$ is R$^1$. In some other embodiments, R$^{11}$ is R$^1$—Z—(CH$_2$)$_m$—. In some embodiments, R$^{11}$ is R$^1$—Z—(CH$_2$)$_m$—, and Z is NH. In some other embodiments, R$^{11}$ is R$^1$—Z—(CH$_2$)$_m$—, and Z is O. In yet some other embodiments, R$^{11}$ is R$^1$—Z—(CH$_2$)$_m$—, Z is NH, m is 2.

In some embodiments, R$^2$ is H. In some embodiments, R$^2$ is CH$_3$. In yet some other embodiments, R$^2$ is CH$_3$CH$_3$, CH$_2$CH$_2$CH$_3$, or CH(CH$_3$)$_2$.

In some embodiments, Y is —NR$_4$R$_5$R$_6$$^{(+)}$. In some other embodiments, Y is —NR$_4$R$_5$R$_6$$^{(+)}$, and R$^4$, R$^5$, and R$^6$ are independently CH$_3$. In yet some other embodiments, Y is —NR$_4$R$_5$R$_6$$^{(+)}$, and R$^4$ and R$^5$, independently CH$_3$, and R$^6$ is a C$_6$-C$_{12}$ aromatic alkyl. In some other embodiments, Y is —NR$_4$R$_5$R$_6$$^{(+)}$, and R$^4$ and R$^5$, independently CH$_3$, and R$^6$ is —CH$_2$—C$_6$H$_6$.

In some embodiments, Y is —NR$_4$R$_5$R$_6$$^{(+)}$ and the counter ion for Y is any negative charged ion or species. In some other embodiments, the counter ion for Y is chloride, bromide, fluoride, iodide, acetate, aluminate, cyanate, cyanide, dihydrogen phosphate, dihydrogen phosphite, formate, carbonate, hydrogen carbonate, hydrogen oxalate, hydrogen sulfate, hydroxide, nitrate, nitrite, thiocyanate, or a combination thereof.

In some embodiments, R$^3$ is CH$_2$. In some other embodiments, R$^3$ is CH$_2$CH$_2$. In other embodiments, R$^3$ is C(CH$_3$)$_2$. In yet some other embodiments, R$^3$ is an unsubstituted, linear, and saturated C$_2$-C$_{10}$ alkylene group. In some embodiments, R$^3$ is an unsubstituted, linear, and unsaturated C$_2$-C$_{10}$ alkylene group.

In some embodiments, R$^1$ is a linear C$_1$-C$_{30}$ alkyl, alkenyl, or alkynyl group. In some other embodiments, R$^1$ is a branched C$_1$-C$_{30}$ alkyl, alkenyl, or alkynyl group. In yet some embodiments, R$^1$ is a linear and saturated C$_5$-C$_{30}$ alkyl group. In some other embodiments, R$^1$ is a branched and saturated C$_5$-C$_{30}$ alkyl group.

In some embodiments, R$^1$ is a linear C$_1$-C$_{30}$ alkenyl group with one or more double bonds. In some other embodiments, wherein R$^1$ is a branched C$_1$-C$_{30}$ alkenyl group with one or more double bonds.

In some embodiments, R$^1$ is a linear C$_1$-C$_{30}$ alkynyl group with one or more triple bonds. In some other embodiments, R$^1$ is a branched C$_1$-C$_{30}$ alkynyl group with one or more triple bonds.

In some embodiments, R$^{11}$ is a linear and saturated C$_2$-C$_{20}$ alkyl group. In some other embodiments, R$^{11}$ is a trans C$_2$-C$_{20}$ alkenyl group with at least one double bond. In some other embodiments, R$^{11}$ is a C$_2$-C$_{20}$ alkenyl group with at least one double bond of trans configuration. In some embodiments, R$^{11}$ is a cis C$_2$-C$_{20}$ alkenyl group with at least one double bond. In some other embodiments, R$^{11}$ is a C$_2$-C$_{20}$ alkenyl group with at least one double bond of cis configuration.

In some embodiments, R$^{11}$ is R$^1$—NH—CH$_2$CH$_2$CH$_2$ group and R$^1$ is a linear and saturated C$_2$-C$_{20}$ alkyl, a trans alkenyl, or a cis alkenyl group.

In some other embodiments, R$^2$ is H, X is NH, R$^3$ is CH$_2$CH$_2$, Y is CH$_2$—N$^+$(CH$_3$)$_3$Cl$^-$.

In another aspect, disclosed herein is a compound according to Formula II or Formula III

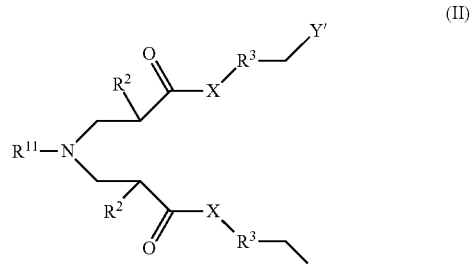

(II)

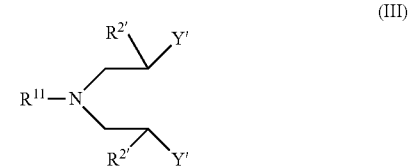

(III)

wherein X is NH, or O; R$^{11}$ is R$^1$ or R$^1$—Z—(CH$_2$)$_m$—; R$^1$ is an unsubstituted or substituted, linear or branched C$_1$-C$_{30}$ alkyl, cyclic alkyl, alkenyl, or alkynyl group; Z is NH or O; R$^2$ is H, CH$_3$, or an unsubstituted, linear or branched C$_1$-C$_{10}$ alkyl, alkenyl, or alkynyl group; R$^{2'}$ is H, CH$_3$, or an unsubstituted or substituted, linear or branched C$_1$-C$_{10}$ alkyl, alkenyl, alkynyl group, —COOH, —CH$_2$COOH, Y', or —(CH$_2$)$_m$—Y'; m is an integer of 1 to 4; R$^3$ is absent or an unsubstituted, linear C$_1$-C$_{30}$ alkylene group; Y' is —COOH, —PO$_3$H, —OPO$_3$H, —SO$_3$H, —OSO$_3$H or salt thereof.

In some embodiments, Y' is —COOH or salt thereof. In some embodiments, Y' is —PO$_3$H, —OPO$_3$H, or salt thereof. In some other embodiments, Y' is —SO$_3$H, —OSO$_3$H, or salt thereof.

In some embodiments of the disclosed compounds herein, X is NH. In some other embodiments, X is O.

In some embodiments, R$^{11}$ is R$^1$. In some other embodiments, R$^{11}$ is R$^1$—Z—(CH$_2$)$_m$—. In some embodiments, R$^{11}$ is R$^1$—Z—(CH$_2$)$_m$—, and Z is NH. In some other embodiments, $R^{11}$ is $R^1$—Z—$(CH_2)_m$—, and Z is O. In yet some other embodiments, $R^{11}$ is $R^1$—Z—$(CH_2)_m$—, Z is NH, m is 2.

In some embodiments, $R^2$ is H. In some embodiments, $R^2$ is $CH_3$. In yet some other embodiments, $R^2$ is $CH_3CH_3$, $CH_2CH_2CH_3$, or $CH(CH_3)_2$.

In some embodiments, $R^{2'}$ is H. In some embodiments, $R^{2'}$ is $CH_3$. In yet some other embodiments, $R^{2'}$ is $CH_3CH_3$, $CH_2CH_2CH_3$, or $CH(CH_3)_2$. In some other embodiments, $R^{2'}$ is —COOH. In some other embodiments, $R^{2'}$ is —$CH_2$COOH.

In some embodiments, $R^3$ is $CH_2$. In some other embodiments, $R^3$ is $CH_2CH_2$. In other embodiments, $R^3$ is $C(CH_3)_2$. In yet some other embodiments, $R^3$ is an unsubstituted, linear, and saturated $C_2$-$C_{10}$ alkylene group. In some embodiments, $R^3$ is an unsubstituted, linear, and unsaturated $C_2$-$C_{10}$ alkylene group.

In some embodiments, $R^1$ is a linear $C_1$-$C_{30}$ alkyl, alkenyl, or alkynyl group. In some other embodiments, $R^1$ is a branched $C_1$-$C_{30}$ alkyl, alkenyl, or alkynyl group. In yet some other embodiments, $R^1$ is a linear and saturated $C_5$-$C_{30}$ alkyl group. In some other embodiments, $R^1$ is a branched and saturated $C_5$-$C_{30}$ alkyl group.

In some embodiments, $R^1$ is a linear $C_1$-$C_{30}$ alkenyl group with one or more double bonds. In some other embodiments, wherein $R^1$ is a branched $C_1$-$C_{30}$ alkenyl group with one or more double bonds.

In some embodiments, $R^1$ is a linear $C_1$-$C_{30}$ alkynyl group with one or more triple bonds. In some other embodiments, $R^1$ is a branched $C_1$-$C_{30}$ alkynyl group with one or more triple bonds.

In some embodiments, $R^{11}$ is a linear and saturated $C_2$-$C_{20}$ alkyl group. In some other embodiments, $R^{11}$ is a trans $C_2$-$C_{20}$ alkenyl group with at least one double bond. In some other embodiments, $R^{11}$ is a $C_2$-$C_{20}$ alkenyl group with at least one double bond of trans configuration. In some embodiments, $R^{11}$ is a cis $C_2$-$C_{20}$ alkenyl group with at least one double bond. In some other embodiments, $R^{11}$ is a $C_2$-$C_{20}$ alkenyl group with at least one double bond of cis configuration.

In some embodiments, $R^{11}$ is $R^1$—NH—$CH_2CH_2CH_2$ group and $R^1$ is a linear and saturated $C_1$-$C_{20}$ alkyl, a trans alkenyl, or a cis alkenyl group.

In some other embodiments, $R^2$ is H, X is NH, $R^3$ is $CH_2CH_2$, Y' is —COOH or —$PO_3$H. In some embodiments, the compound is one by Formula II. In some other embodiments, the compound is one by Formula III.

In some embodiments, the compound is one with formula III, $R^{2'}$ is H, X is NH, Y' is —COOH or —$PO_3$H. In some other embodiments, the compound is one with formula III, $R^{2'}$ is —$CH_3$, X is NH, Y' is —COOH or —$PO_3$H. In yet some other embodiments, the compound is one with formula III, $R^{2'}$ is Y' or —$CH_2$Y', X is NH, Y' is —COOH or —$PO_3$H.

In yet some other embodiments, when the compound is one with formula III and the Y' group is negatively charged, the counter positive ions for the negative charges include, but are not limited to, alkali metal ions, $Li^+$, $Na^+$, $K^+$, $NH_4^+$, a quaternary ammonium ion, etc.

Without being limited to a particular mechanism of action or definition of structure and function of the compounds, the compounds disclosed herein have two hydrophilic groups associated with one hydrophobic group. Accordingly, the compounds disclosed herein have a ratio of hydrophilic groups to hydrophobic group of 2:1 as compared to both a conventional surfactant and Gemini surfactant, which exhibit a 1:1 ratio. FIG. 1A, FIG. 1B, and FIG. 1C shows a representation of an exemplary compound disclosed herein (FIG. 1C), together with ones for a conventional (FIG. 1A) and Gemini surfactant (FIG. 1B). Due to the higher ratio of hydrophilic groups to hydrophobic group, the disclosed compounds are particularly well suited for use as antimicrobial sanitizers, fabric softeners, antistatic agents, corrosion inhibitors, foaming agents, floatation collectors, dispersants, surfactants assisted enhanced oil recovery (EOR), cleaners, etc.

In this disclosure, the term "hydrophobic group" can be used interchangeable with the term "hydrophobic tail or head." Similarly, the term "hydrophilic group" can be used interchangeably with the term "polar head or tail", or "hydrophilic group", or "polar group." The term "a molecule" can also be used interchangeably with the term "a compound."

Methods of Making

In another aspect, disclosed herein is a method to synthesize the compounds disclosed herein. The disclosed method comprises contacting a primary amine (Michael donor) with an activated olefin containing a hydrophilic group (Michael acceptor) at a temperature of from about −20° C. to about 200° C., in some embodiments, for from about 10 minutes to about 48 hours, to generate the compounds disclosed herein. The reaction leading to the compounds disclosed herein is aza-Michael addition between a primary amine (Michael donor) and an activated olefin containing a hydrophilic group (Michael acceptor).

An aliphatic amine group may undergo an aza-Michael Addition reaction when in contact with an unsaturated hydrocarbon moiety (e.g., carbon-carbon double bond) that is in proximity of an electron withdrawing group such as carbonyl, cyano, or nitro group. Specifically, the Michael addition is a reaction between nucleophiles and activated olefin and alkyne functionalities, wherein the nucleophile adds across a carbon-carbon multiple bond that is adjacent to an electron withdrawing and resonance stabilizing activating group, such as a carbonyl group. The Michael addition nucleophile is known as the "Michael donor", the activated electrophilic olefin is known as the "Michael acceptor", and reaction product of the two components is known as the "Michael adduct." Examples of Michael donors include, but are not restricted to, amines, thiols, phosphines, carbanions, and alkoxides. Examples of Michael acceptors include, but are not restricted to, acrylate esters, alkyl methacrylates, acrylonitrile, acrylamides, maleimides, cyanoacrylates and vinyl sulfones, vinyl ketones, nitro ethylenes, α, β-unsaturated aldehydes, vinyl phosphonates, acrylonitrile, vinyl pyridines, azo compounds, beta-keto acetylenes and acetylene esters.

As used herein, an "activated olefin" refers to a substituted alkene in which at least one of the double-bond carbon has a conjugated electron withdrawing group. Examples of activated olefins include, but not limited to, α, β-unsaturated carbonyl compounds (such as $CH_2$=CHCO—NH—$CH_3$, alkyl-CH=CH—CO-alkyl, $CH_2$=$CH_2$C(O)—O—$CH_3$), $CH_2$=CH—COOH, $CH_2$=$CH(CH_3)$—COOH, $CH_2$=CH—$SO_3$H, and like.

As used herein, "contacting" is referred to any way to bring the primary amine (Michael donor) and the activated olefin containing at least one cationic or anionic group (Michael acceptor) together as one skilled in the art would do to conduct a chemical reaction in a controlled and practical manner. For example, in some embodiments, the primary amine or a solution comprising the primary amine can be added into a container or vessel containing the activated olefin or a solution comprising the activated olefin, in batches or drops. In some other embodiments, the activated olefin or a solution comprising the activated olefin can be added into a container or vessel containing the primary amine or a solution comprising the primary amine, in batches or drops. In yet some other embodiments, both the activated olefin or a solution comprising the activated olefin and the primary amine or a solution comprising the primary amine are added to a container or vessel in batches or drops, simultaneously, sequentially, or alternatively.

The chemical reaction used to synthesize the disclosed compounds is Aza-Michael addition reaction. It was found that the Aza-Michael addition can be used to synthesize the disclosed compounds under mild conditions and a high yield for the disclosed compounds in a reasonable reaction time.

Aza-Michael addition reaction can be catalyzed by a strong acid or base. In some cases, some ionic liquids can function both as reaction media and catalyst. The preferred catalyst for the Aza-Michael addition reaction to synthesize the disclosed compounds is a base. The base catalyst can be any or a combination of an alkalinity source or primary alkalinity source. Exemplary base catalyst can be an alkali metal, hydroxide, alkali metal carbonate, alkali metal silicate, alkali metal silicate, or amine. Exemplary base catalyst can be hydroxide and amines. Because the reaction to synthesize the disclosed compounds uses a primary amine, the primary amine itself can function as a catalyst for the reaction. In such embodiments, no additional catalyst is necessary, or an additional catalyst is optional. Other preferred catalysts include amidine and guanidine bases.

The use of solvent and/or diluent for the reaction is optional. When employed, a wide range of non-acidic solvents are suitable, such as, for example, water, ethers (e.g., tetrahydrofuran (THF)), aromatic hydrocarbons (e.g., toluene and xylene), alcohols (e.g., n-butanol), esters (e.g., ethyl 3-ethoxypropionate), and the like. A wide range of solvents can be used for the reaction because the synthesis process is relatively insensitive to solvent. When solvent (or diluent) is employed, loading levels can range from about 0 wt-% up to about 80 wt-% and higher. The solvent loading level can be about 0 wt-%, from about 1 wt-% to about 10 wt-%, from about 10 wt-% to about 20 wt-%, from about 20 wt-% to about 30 wt-%, from about 30 wt-% to about 40 wt-%, from about 40 wt-% to about 50 wt-%, from about 50 wt-% to about 60 wt-%, from about 60 wt-% to about 70 wt-%, from about 70 wt-% to about 80 wt-%, from about 1 wt-% to about 20 wt-%, from about 20 wt-% to about 40 wt-%, from about 40 wt-% to about 60 wt-%, from about 60 wt-% to about 80 wt-%, from about 40 wt-% to about 70 wt-%, about 5 wt-%, about 15 wt-%, about 25 wt-%, about 35 wt-%, about 45 wt-%, about 55 wt-%, about 65 wt-%, about 75 wt-%, or any value there between of the final reaction mixture.

Generally, the contacting step of the method can be carried out at a temperature over a wide range of temperatures. The contacting, or reaction temperature can range from about −20° C. to about 200° C., from about 0° C. to about 150° C., more preferably from about 50° C. to about 80° C. The contacting temperature can be from about 10° C. to about 140° C., about 20° C. to about 130° C., about 30° C. to about 120° C., about 40° C. to about 110° C., about 50° C. to about 100° C., about 60° C. to about 90° C., about 70° C. to about 80° C., about 0° C. to about 20° C., about 20° C. to about 40° C., about 40° C. to about 60° C., about 60° C. to about 80° C., about 80° C. to about 100° C., about 100° C. to about 120° C., about 120° C. to about 150° C., about 5° C., about 25° C., about 45° C., about 65° C., about 85° C., about 105° C., about 125° C., about 145° C., or any value there between. The reaction temperature can be about the same from starting of the reaction to end of the reaction and can be changed from one temperature to another while the reaction is going on.

The contacting or reaction time for the synthesis of the compounds disclosed herein can vary widely, depending on such factors as the reaction temperature, the efficacy and amount of the catalyst, the presence or absence of diluent (solvent), and the like. The preferred reaction time can be from about 10 minutes to about 48 hours, from about 0.5 hours to about 48 hours, from about 1 hour to 40 hours, from about 2 hours to 38 hours, from about 4 hours to about 36 hours, from 6 hours to about 34 hours, from about 8 hours to about 32 hours, from about 10 hours to about 30 hours, from about 12 hours to about 28 hours, from about 14 hours to 26 hours, from about 16 hours to 24 hours, from about 18 hours to 20 hours, from about 1 hour to 8 hours, from 8 hours to 16 hours, from 8 hours to about 24 hours, about 2 hours, about 4 hours, about 6 hours, about 8 hours, about 10 hours, about 14 hours, about 16 hours, about 18 hours, about 24 hours, about 30 hours, about 36 hours, or any values there between.

The reaction for the synthesis of the compounds disclosed herein can go to completion when one mole of the primary amine and at least two moles of the activated olefin, are mixed together for a sufficient of time at a temperature described above. Typically, if the reaction is carried out at a room temperature, the reaction can have a product yield of more than 98%.

In some embodiments of the disclosed methods, the primary amine is $R^{11}$—$NH_2$, $R^{11}$ is $R^1$ or $R^1$—Z—$(CH_2)_m$—; the activated olefin is

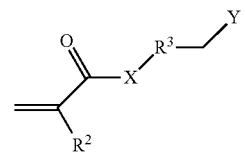

X is NH, or O;
$R^{11}$ is $R^1$ or $R^1$—Z—$(CH_2)_m$—;
$R^1$ is an unsubstituted or substituted, linear or branched $C_1$-$C_{30}$ alkyl, cyclic alkyl, alkenyl, or alkynyl group;
Z is NH or O;
$R^2$ is H, $CH_3$, or an unsubstituted, linear or branched $C_1$-$C_{10}$ alkyl, alkenyl, or alkynyl group;
m is an integer of 1 to 4;
$R^3$ is absent or an unsubstituted, linear $C_1$-$C_{30}$ alkylene group;
Y is —$NR_4R_5R_6^{(+)}$ or a salt thereof; and
$R^4$, $R^5$, and $R^6$ are independently $C_1$-$C_{10}$ alkyl group.

In some embodiments, the activated olefin activated olefin is (3-Acrylamidopropyl)trimethylammonium chloride (APTAC), [3m-(methacryloylamino)propyl]trimethylammonium chloride (MAPTAC), 2-(acryloyloxy)-N,N,N-trimethylethanaminium chloride (DMAEA-MCQ), N,N-dimethylaminoethyl acrylate benzyl chloride quaternary salt (DMAEA-BCQ), 2-(methacryloyloxy)-N,N,N-trimethylethan-1-aminium methyl sulfate (DMAEA-MSQ), 2-(acryloyloxy)-N,N,N-trimethylethanaminium chloride (DMAEA-MSQ), or mixture thereof.

In some embodiments of the disclosed methods, the primary amine is $R^{11}$—$NH_2$, $R^{11}$ is $R^1$ or $R^1$—Z—$(CH_2)_m$—; the activated olefin is

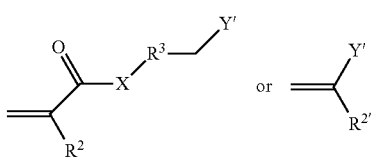

X is NH, or O;

$R^{11}$ is $R^1$ of $R^1$—Z—$(CH_2)_m$—;

$R^1$ is an unsubstituted or substituted, linear or branched $C_1$-$C_{30}$ alkyl, cyclic alkyl, alkenyl, or alkynyl group;

Z is NH or O;

$R^2$ is H, $CH_3$, or an unsubstituted, linear or branched $C_1$-$C_{10}$ alkyl, alkenyl, or alkynyl group;

$R^{2'}$ is H, $CH_3$, or an unsubstituted or substituted, linear or branched $C_1$-$C_{10}$ alkyl, alkenyl, alkynyl group, —COOH, —$CH_2$COOH, Y', or —$(CH_2)_m$—Y';

m is an integer of 1 to 4;

$R^3$ is absent or an unsubstituted, linear $C_1$-$C_{30}$ alkylene group; and

Y' is —COOH, —$PO_3H$, —$SO_3H$, —$OSO_3H$, —$OPO_3H$, or a salt thereof.

In some embodiments, the activated olefin is acrylic acid, methacrylic acid, itaconic acid, maleic acid, vinylsulfonic acid, vinylphosphonic acid, or mixture thereof.

In some other embodiments, the activated olefin is 2-acrylamido-2-methylpropane sulfonic acid (AMPS), 3-(allyloxy)-2-hydroxypropane-1-sulfonate, or mixture thereof.

In yet some other embodiments, when the activated olefin contains anionic group that can bear negative charge at an alkaline pH, the counter positive ions for the negative charges include, but are not limited to, alkali metal ions, $Li^+$, $Na^+$, $K^+$, $NH_4^+$, a quaternary ammonium ion, etc.

In some embodiments of the disclosed methods, the contacting step is done in the presence of a reaction solvent. The reaction solvent can be any inorganic or organic solvent commonly used in chemical synthesis. The reaction solvent used in the disclosed method can be introduced into the reaction between the primary amine and the activated olefin including a cationic or anionic group by any way known by one skilled in the art. For example, the solvent can be added into the container or vessel for reaction before, at the same, with one or both reactants, or after the primary amine, the activated olefin, or both are added.

In some embodiments, the reaction solvent is water, methanol, ethanol, propanol, glycol, PEG, or a mixture thereof. In some other embodiments, the reaction solvent is water.

In some other embodiments of the disclosed methods, the contacting step is done in the presence of a catalyst, base, or acid. The catalyst, base, or acid can be introduced into the reaction between the primary amine and activated olefin by any way known by one skilled in the art.

In some embodiments, the contacting step is done without the presence of any additional base. In some other embodiments, the contacting step is done in the presence of an alkalinity source. In some other embodiments, the contacting step is done in the presence of an organic base, such as alkanolamines. In yet some other embodiments, the contacting step is done in the presence of an alkali metal hydroxide, carbonate, imidazole/pyridine based base, or combination thereof, such as NaOH, $Na_2CO_3$, aminoethyl pyridine, aminopropyl imidazole, or a combination thereof. In some other embodiments, the contacting step is done with the presence of benzyltrimethylammonium hydroxide. In some embodiments, the catalyst base is an amidine or guanidine base, or mixtures thereof. In some other embodiments, the catalyst is a ionic liquid, such as 1,8-diazabicyclo[5.4.0]-undec-7-en-8-ium acetate, for the reaction under a solvent free condition at room temperatures.

In yet some other embodiments of the disclosed methods, the contacting step is done in the presence of an acid. In some other embodiments, the contacting step is done in the presence of a catalyst. The catalyst can any one or more of the catalysts known for the Michael addition reaction by one skilled in the art.

In yet some other embodiments of the disclosed methods, the contacting step is done free of a catalyst, base, or acid. In some other embodiments, the contacting step is done free of an alkali metal hydroxide, carbonate, silicate, metasilicate, imidazole/pyridine-based base, or all thereof. In some embodiments, the contact step is done free of a base.

In yet another aspect, disclosed herein is an article, product, or composition comprising one or more compounds disclosed here or produced by the methods disclosed herein.

In some embodiments, the article, product or composition further comprises a carrier solvent or a carrier. As used herein, a "carrier solvent" or carrier is a solvent or solvent system in which the disclosed compound can be distributed evenly and stable.

As used herein, "stable" means that compounds disclosed herein does not precipitate from or separated from the carrier solvent or other ingredients in the composition in about 1 hour, from about 1 hour to about 12 hours, about 12 hours, about 1 day, about 5 days, about 10 days, about 20 days, about 1 month, from about 1 month to about 1 year, or from about 1 year to about 2 year after the compounds disclosed herein and carrier solvent or any other ingredients are mixed homogenously.

In some embodiments, the carrier solvent can be any inorganic or organic solvent commonly used in industry or in laboratory. In some other embodiments of the article, product, or composition, the carrier solvent is water, an alcohol, an alkylene glycol, an alkyleneglycol alkyl ether, or a combination thereof. In some other embodiments, the carrier solvent is methanol, ethanol, propanol, isopropanol, butanol, isobutanol, monoethyleneglycol, ethyleneglycol monobutyl ether, or a combination thereof.

In some embodiments, the articles, products, or compositions are solid. In some other embodiments, the articles, products, or compositions are liquid.

In some embodiments, the article, product or composition can further comprise an additional surfactant. The additional surfactant is a nonionic, semi-nonionic, anionic, cationic, amphoteric, zwitterionic, Gemini surfactant, or combinations thereof.

In some embodiments, the additional surfactant is a nonionic, semi-nonionic, anionic, cationic, amphoteric, zwitterionic, Gemini surfactant, or combinations thereof. In some embodiments, the composition disclosed here includes a normal surfactant but is free of a Gemini surfactant. In some other embodiments, the composition includes a Gemini surfactant, but is free of a normal surfactant. In yet some other embodiments, the surfactant composition includes one kind of nonionic, semi-nonionic, anionic, cationic, amphoteric, and zwitterionic surfactants, but is free of the rest of the surfactants. For example, a disclosed composition can include one or more compounds disclosed herein and one or more nonionic surfactants, but is free of a semi-nonionic, anionic, cationic, amphoteric, zwitterionic, or Gemini surfactant.

In some embodiments, the article, product or composition disclosed here comprises one or more compounds disclosed herein, an acid, and carrier solvent. In some embodiments, the article, product or composition disclosed here comprises one or more compounds disclosed herein, an acid, carrier solvent, and a peroxycarboxylic acid or peroxycarboxylic acid composition.

In some embodiments, the article, product or composition can further comprise a primary alkalinity source. In some embodiments, the article, product or composition disclosed here is a detergent composition that comprises one or more compounds disclosed herein and primary alkalinity sources. A detergent composition, as used herein, refers to a composition that contains more primary alkalinity source than the compounds disclosed herein in weight percentage and can generate an alkaline use solution having a use solution pH of from about 8 to about 13.

In some embodiments, the article, product or composition disclosed here is a detergent composition that comprises one or more compounds disclosed herein, primary alkalinity sources, and chelants. In some embodiments, the article, product or composition disclosed here is a detergent composition that comprises one or more compounds disclosed herein, primary alkalinity sources, chelants, and surfactants. In some embodiments, the article, product or composition disclosed here is a detergent composition that comprises one or more compounds disclosed herein, primary alkalinity sources, and chelants, but is free of a surfactant.

In some embodiments, the compositions are solid compositions. In some other embodiments, the compositions are liquid.

In some embodiments, the article, product or composition disclosed here is a detergent composition that comprises one or more compounds disclosed herein, primary alkalinity sources, and enzymes. In some embodiments, the article, product or composition disclosed here is a detergent composition that comprises one or more compounds disclosed herein, primary alkalinity sources, chelants, enzymes, and surfactants. In some embodiments, the article, product or composition disclosed here is a detergent composition that comprises one or more compounds disclosed herein, primary alkalinity sources, and enzymes, but is free of a surfactant, chelant, or both.

In some embodiments, the primary alkalinity source comprises an alkali metal hydroxide, alkali metal carbonate, alkali metal silicate, alkali metal silicate, amine, or mixture thereof. In some other embodiments, the primary alkalinity source comprises an alkali metal hydroxide, alkali metal carbonate, or mixture thereof. In some embodiments, the detergent composition disclosed herein include a builder. In some embodiments, the detergent composition disclosed herein is free of a builder but includes a part of the primary alkalinity source as builder.

In some embodiments, the detergent composition disclosed herein include an enzyme, wherein the enzyme is amylase, protease, lipase, cellulase, cutinase, gluconase, peroxidase, and/or mixtures thereof. In some embodiments, the enzyme is a protease enzyme. In some other embodiments, the enzyme is a protease and amylase. In some other embodiments, the enzyme is a protease, amylase, and a lipase. In yet some other embodiments, the detergent composition or composition disclosed herein is free of an enzyme.

In some embodiments, the detergent composition or composition disclosed here include a chelant, wherein the chelant is methylglycinediacetic acid (MGDA), glutamic acid-N,N-diacetic acid (GLDA), N-hydroxyethylaminodiacetic acid, ethylenediaminetetraacetic acid (EDTA) (including tetra sodium EDTA), hydroxyethylenediaminetetraacetic acid, diethylenetriaminepentaacetic acid, N-hydroxyethyl-ethylenediaminetriacelic acid (HEDTA), diethylenetri-aminepentacetic acid (DTPA), ethylenediaminesuccinic acid (EDDS), 2-hydroxyethyliminodiacetic acid (HEIDA), imi-nodisuccinic acid (IDS), 3-hydroxy-2-2'-iminodisuccinic acid (HIDS), or a mixture thereof.

In other embodiments, the detergent composition disclosed herein further include one or more addition detergent composition agents.

In some embodiments, the detergent compositions disclosed herein are solid compositions. In some other embodiments, the detergent compositions are liquid. In some embodiments, the solid detergent compositions disclosed herein are any pressed, extruded, or cast solid compositions, or in loose powder forms. In some other embodiments, the solid detergent composition is pressed and/or extruded blocks. In some other embodiments, the detergent compositions are multiple-use pressed solid block compositions.

A multi-use solid block detergent composition is preferred because the solid block detergent composition provides solid state stability and can be used in a dispenser. The use of solidification technology and solid block detergents for institutional and industrial operations is set forth for example with respect to the SOLID POWER® brand technology such as disclosed in U.S. Reissue Pat. Nos. 32,762 and 32,818. In some embodiments, the detergent compositions disclosed herein include sodium carbonate hydrate cast solid products as disclosed by Heile et al., U.S. Pat. Nos. 4,595,520 and 4,680,134. Each of these references are herein incorporated by reference in its entirety. Without being limited according to a mechanism of action, the solidification mechanism is ash hydration or the interaction of the sodium carbonate with water.

The methods and compositions of the present disclosure may comprise, consist essentially of, or consist of the components and ingredients of the disclosed compositions or methods as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Alkalinity Source

The disclosed methods of preparation may include using an effective amount of an alkalinity source as a catalyst. The alkalinity source in turn comprises one or more alkaline compounds. The alkalinity source can be added to the reaction mixture in the form of solid, liquid, or solution thereof.

In general, an effective amount of the alkalinity source should be considered as an amount that provides a reaction mixture having a pH of at least about 8. When the solution has a pH of between about 8 and about 10, it can be considered mildly alkaline, and when the pH is greater than about 12, the solution can be considered caustic.

The alkalinity source can include an alkali metal carbonate, an alkali metal hydroxide, alkaline metal silicate, alkaline metal metasilicate, or a mixture thereof. Suitable metal carbonates that can be used include, for example, sodium or potassium carbonate, bicarbonate, sesquicarbonate, o r a mixture thereof. Suitable alkali metal hydroxides that can be used include, for example, sodium, lithium, or potassium hydroxide. Examples of useful alkaline metal silicates include sodium or potassium silicate (with $M_2O:SiO_2$ ratio of 2.4 to 5:1, M representing an alkali metal) or metasilicate. A metasilicate can be made by mixing a hydroxide and silicate. The alkalinity source may also include a metal borate such as sodium or potassium borate, and the like.

The alkalinity source may also include ethanolamines, urea sulfate, amines, amine salts, and quaternary ammonium. The simplest cationic amines, amine salts and quaternary ammonium compounds can be schematically drawn thus:

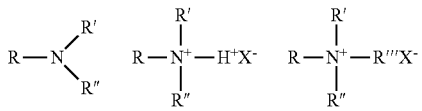

in which, R represents a long alkyl chain, R', R", and R'" may be either long alkyl chains or smaller alkyl or aryl groups or hydrogen and X represents an anion.

In some embodiments, the methods of preparation are free of the alkalinity source because the reactants contain a primary amine or primary amine group to catalyze the reaction.

Primary Alkalinity Source

The disclosed composition can include a primary alkalinity source, especially when the disclosed composition is a detergent composition.

The primary alkalinity source of the composition or detergent composition disclosed herein can include, for example, an alkali metal hydroxide, alkali metal carbonate, alkali metal silicate, alkali metal metasilicate or mixture thereof. Examples of suitable alkalinity sources include, but are not limited to, sodium hydroxide, potassium hydroxide, sodium carbonate, potassium carbonate, sodium silicate, sodium metasilicate, potassium silicate, or a mixture thereof. The alkalinity source is preferably an alkali hydroxide, alkali carbonate, or mixture thereof. The alkalinity source controls the pH of the resulting use solution of the composition disclosed when water or other diluent is added to the composition to form a use solution.

When the disclosed composition is a detergent composition, the pH of the use solution must be maintained in the alkaline range to provide sufficient detergency properties. Therefore, the disclosed detergent composition comprises more primary alkalinity source than the disclosed compounds disclosed herein in term of weight percentage.

A use solution of a composition disclosed herein as used herein refers to a diluted solution for the composition or compounds by a diluent. A diluent as used herein refers to water, city water, distilled water, or carrier solvents defined herein. The composition or the compounds can be diluted by a factor of 0.5, 1, 2, 3, 4, 5, 6, 7, 8, 9, 10, 11-1,000,000, or any value there between to generate a use solution and then use the use solution for this application. In this disclosure, when a composition or di-cationic compounds are applied, either the composition/compounds or use solution thereof is applied.

When the disclosed composition is a detergent composition, the pH of a use solution of the detergent composition is defined as the pH that is determined at room temperature when the use solution is obtained by diluting the detergent composition with distilled water and contains from 0.1 g/L to about 3 g/L of the primary alkalinity source. In some embodiments, the concentration of the alkalinity source is from about 0.1 g/L to about 0.5 g/L, from about 0.5 g/L to about 1 g/L, from about 1 g/L to about 3 g/L, from about 1 g/L to about 2 g/L, from about 2 g/L to about 3 g/L, about 0.1 g/L, about 0.2 g/L, about 0.3 g/L, about 0.4 g/L, about 0.5 g/L, about 1.0 g/L, about 1.5 g/L, about 2.0 g/L, about 2.5 g/L, about 3.0 g/L, or any value there between in the use solution.

Alternatively, when the disclosed composition is a detergent composition, the pH of a use solution of the detergent composition is defined as the pH that is determined at room temperature when the use solution is obtained by diluting the detergent composition with distilled water and contains from 0.5 g/L to about 5 g/L of the composition. In some embodiments, the concentration of the composition is from about from about 0.5 g/L to about 1 g/L, from about 1 g/L to about 2 g/L, from about 2 g/L to about 3 g/L, from about 3 g/L to about 4 g/L, from about 4 g/L to about 5 g/L, about 0.5 g/L, about 1.0 g/L, about 1.5 g/L, about 2.0 g/L, about 2.5 g/L, about 3.0 g/L, about 3.5 g/L, about 4.0 g/L, about 4.5 g/L, about 5.0 g/L or any value there between in the use solution.

In some embodiments, a use solution of the detergent composition therefore provides a pH of at least about 8, preferably a pH of from about 9.5 to about 12, more preferably from about 10 to about 11 or from about 11 to about 12, when its primary alkalinity source is at a concentration of about 0.1 g/L, about 0.2 g/L, about 0.5 g/L, about 0.8 g/L, or about 1 gram per liter (g/L). In some embodiments, a use solution of the detergent composition therefore provides a pH of at least 8, preferably a pH of 9.5 to 11, more preferably 10 to 11, from about 11 to about 12, when its primary alkalinity source in distilled water is at a concentration of about 1 g/L, about 1.5 g/L, about 2.0 g/L, about 2.5 g/L, about 3 g/L, or any value there between.

In some other embodiments, a use solution of the detergent composition therefore provides a pH of at least about 8, preferably a pH of from about 9.5 to about 12, more preferably from about 10 to about 11 or from about 11 to about 12, when the composition itself is at a concentration of about 0.5 g/L, about 0.8 g/L, about 1 g/L, about 1.5 g/L, about 2.0 g/L, about 2.5 g/L, about 3.0 g/L, about 3.5 g/L, about 4.0 g/L, about 4.5 g/L, or about 5.0 g/L. In some embodiments, a use solution of the detergent composition therefore provides a pH of at least 8, preferably a pH of 9.5 to 11, more preferably 10 to 11, from about 11 to about 12, when the composition itself is at a concentration of about 1 g/L, about 1.5 g/L, about 2.0 g/L, about 2.5 g/L, about 3 g/L, about 3.5 g/L, about 4.0, g/L, about 4.5 g/L, about 5.0 g/L, or any value there between.

In some embodiments, the pH of the use solution is between about 10 and about 13. In some embodiments, the pH of the use solution is between about 8 and about 10. Particularly, the pH of the use solution is about 11-12. If the pH of the use solution is too low, for example, below approximately 10, the use solution may not provide adequate detergency properties. Further, at lower pH levels, the silicate species become unstable and may precipitate out of solution. If the pH of the use solution is too high, for example, above approximately 13, the use solution may be too alkaline and attack or damage the surface to be cleaned. A further consideration for the pH is that if the composition is too alkaline, a user would be required to wear PPE. However, if the pH of the composition is at or below about 11.5 pH, PPE is not required. Therefore, it is desirable for the pH of the detergent composition disclosed herein in diluted use form to be between about 11 and about 12 for the composition to be effective, but not corrosive to human skin.

Preferably, the primary alkalinity source is an alkali metal hydroxide. Preferred alkali metal hydroxides include sodium hydroxide and potassium hydroxide. More preferably, the primary alkalinity source is sodium hydroxide. Sodium carbonate can be of light density or heavy density.

When a carbonate is included in the disclosed detergent composition, an effective amount of the alkali metal carbonate is an amount that provides a use solution having a pH of at least 8, preferably a pH of 9.5 to 11, more preferably 10 to 10.3.

In general, when the primary alkalinity source is present in the disclosed detergent composition at a concentration of at least about 1 wt-%, the composition or a use solution of the composition can emulsify fats and oils present. When the primary alkalinity source is present in a concentration of about 3 wt-% or greater, the composition or a use solution of the composition can emulsify, suspend, and separate oils and fats after treatment.

In some embodiments where the disclosed composition is not a detergent composition, the composition is free of a primary alkalinity source.

Acids

Generally, acids, as used in this disclosure, include both organic and inorganic acids. Organic acids include, but not limited to, hydroxyacetic (glycolic) acid, formic acid, acetic acid, propionic acid, butyric acid, valeric acid, caproic acid, gluconic acid, itaconic acid, trichloroacetic acid, urea hydrochloride, and benzoic acid. Organic acids also include dicarboxylic acids such as oxalic acid, malonic acid, succinic acid, glutaric acid, maleic acid, fumaric acid, adipic acid, and terephthalic acid. Combinations of these organic acids can also be used. Inorganic acids include, but are not limited to, mineral acids, such as phosphoric acid, sulfuric acid, sulfamic acid, methylsulfamic acid, hydrochloric acid, hydrobromic acid, hydrofluoric acid, and nitric acid. Inorganic acids can be used alone, in combination with other inorganic acid(s), or in combination with one or more organic acid. Acid generators can be used to form a suitable acid, including for example generators such as potassium fluoride, sodium fluoride, lithium fluoride, ammonium fluoride, ammonium bifluoride, sodium silicofluoride, etc.

Examples of particularly suitable acids in this the methods or compositions disclosed herein include inorganic and organic acids. Exemplary inorganic acids include phosphoric, phosphonic, sulfuric, sulfamic, methylsulfamic, hydrochloric, hydrobromic, hydrofluoric, and nitric. Exemplary organic acids include hydroxyacetic (glycolic), citric, lactic, formic, acetic, propionic, butyric, valeric, caproic, gluconic, itaconic, trichloroacetic, urea hydrochloride, and benzoic. Organic dicarboxylic acids can also be used such as oxalic, maleic, fumaric, adipic, and terephthalic acid.

Percarboxylic Acids and Peroxycarboxylic Acid Compositions

A peroxycarboxylic acid (i.e. peracid) or peroxycarboxylic acid composition can be included in the articles, products, or compositions disclosed herein. As used herein, the term "peracid" may also be referred to as a "percarboxylic acid," "peroxycarboxylic acid" or "peroxyacid." Sulfoperoxycarboxylic acids, sulfonated peracids and sulfonated peroxycarboxylic acids are also included within the terms "peroxycarboxylic acid" and "peracid" as used herein. As one of skill in the art appreciates, a peracid refers to an acid having the hydrogen of the hydroxyl group in carboxylic acid replaced by a hydroxy group. Oxidizing peracids may also be referred to herein as peroxycarboxylic acids.

A peracid includes any compound of the formula R—(COOOH)$_n$ in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein.

A peroxycarboxylic acid composition, as used herein, refers to any composition that comprises one or more peracids, their corresponding acids, and hydrogen peroxide or or other oxidizing agents. A peroxycarboxylic acid composition can also include a stabilizer, fluorescent active tracer or compound, or other ingredients, as one skilled in the other would know.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid. Peracids such as peroxyacetic acid and peroxyoctanoic acid may also be used. Any combination of these acids may also be used.

In some embodiments, however, the articles, products, or compositions disclosed herein are free of a peroxycarboxylic acid or peroxycarboxylic acid composition.

Builder

The detergent compositions disclosed herein include one or more builders. In some embodiments, a builder may also serve as a part of the primary alkalinity source in the detergent compositions. In some embodiments, the builder includes a carbonate, hydroxide, metasilicate, or mixture thereof In some embodiments, a carbonate can assist in providing solid detergent compositions, as the carbonate can act as a hydratable salt.

Examples of suitable builders include, but are not limited to alkali metal carbonates, alkali metal hydroxides, and alkali metal silicates. Exemplary alkali metal carbonates that can be used include, but are not limited to, sodium or potassium carbonate, bicarbonate, sesquicarbonate, and mixtures thereof. Exemplary alkali metal hydroxides that can be used include, but are not limited to, sodium or potassium hydroxide. The alkali metal hydroxide may be added to the composition in any form known in the art, including as solid beads, dissolved in an aqueous solution, or a combination thereof. Examples of alkali metal silicates include, but are not limited to, sodium or potassium silicate or polysilicate, sodium or potassium metasilicate and hydrated sodium or potassium metasilicate or a combination thereof.

In some embodiments, the composition is free of a builder.

Chelant

The detergent composition disclosed herein may also include a chelant. Chelants include, but are not limited to, chelating agents (chelators), sequestering agents (sequestrants), detergent builders, and the like. Examples of chelants include, but are not limited to, phosphonates, phosphates, aminocarboxylates and their derivatives, pyrophosphates, polyphosphates, ethylenediamine and ethylenetriamine derivatives, hydroxyacids, and mono-, di-, and tri-carboxylates and their corresponding acids. Other exemplary chelants include aluminosilicates, nitroloacetates and their derivatives, and mixtures thereof.

Suitable aminocarboxylic acids according to the invention include, but are not limited to, methylglycinediacetic acid (MGDA), glutamic acid-N,N-diacetic acid (GLDA), N-hydroxyethylaminodiacetic acid, ethylenediaminetetraacetic acid (EDTA) (including tetra sodium EDTA), hydroxyethylenediaminetetraacetic acid, diethylenetriaminepentaacetic acid, N-hydroxyethyl-ethylenediaminetriacetic acid (HEDTA), diethylenetriaminepentaacetic acid (DTPA), ethylenediaminesuccinic acid (EDDS), 2-hydroxyethylimino-diacetic acid (HEIDA), iminodisuccinic acid (IDS), 3-hydroxy-2-2'-iminodisuccinic acid (HIDS) and other similar acids or salts thereof having an amino group with a carboxylic acid substituent. Additional description of suitable aminocarboxylates suitable for use as chelating agents and/or sequestrants is set forth in Kirk-Othmer, Encyclopedia of Chemical Technology, Third Edition, volume 5, pages 339-366 and volume 23, pages 319-320, the disclosure of which is incorporated by reference herein.

Chelants can be water soluble, and/or biodegradable. Other exemplary chelants include TKPP (tetrapotassium pyrophosphate), PAA (polyacrylic acid) and its salts, phosphonobutane carboxylic acid, Alanine,N,N-bis(carboxymethyl)-,trisodium salt, and sodium gluconate.

In some embodiments, the chelant is free of phosphorus. In some embodiments, the chelant may also serve as a solidifying agent to help form the solid composition, such as sodium salts of citric acid.

Preferably, the chelant is a sodium salt of aminocarboxylates. More preferably, the chelant is methyl glycine diacetic acid (MGDA). Synergistic water conditioning is achieved when using methyl glycine diacetic acid (MGDA) in combination with poly acrylic acids and its salts.

In some embodiments, the composition disclosed herein is free of a chelant, detergent builder, or both. In some embodiments, the composition disclosed herein is free of a chelant, detergent builder, or both that contain phosphorus.

Scale Inhibitor

The reverse emulsion breaker composition can further comprise a scale inhibitor. Suitable scale inhibitors include, but are not limited to, phosphates, phosphate esters, phosphoric acids, phosphonates, phosphonic acids, polyacrylamides, salts of Sacrylamidomethyl propane sulfonate/acrylic acid copolymer (AMPS/AA), phosphinated maleic copolymer (PHOS/MA), mono-, bis- and oligomeric phosphinosuccinic acid (PSO) derivatives, polycarboxylic acid, hydrophobically modified polycarboxylic acid, and salts of a polymaleic acid/acrylic acid/acrylamidomethyl propane sulfonate terpolymer (PMA/AA/AMPS).

In some embodiments, the composition disclosed herein is free of a scale inhibitor.

Enzyme

The compositions or detergent compositions disclosed herein can include an enzyme. An enzyme in the detergent compositions enhances removal of soils, prevents re-deposition, and/or reduces foam during applications of the detergent compositions or their use solutions. The function of an enzyme is to break down adherent soils, such as starch or proteinaceous materials, typically found in soiled surfaces and removed by a detergent composition into a wash water source.

Exemplary types of enzymes which can be incorporated into the detergent compositions disclosed herein include, but are not limited to, amylase, protease, lipase, cellulase, cutinase, gluconase, peroxidase, and/or mixtures thereof. A composition disclosed herein may employ more than one enzyme, from any suitable origin, such as vegetable, animal, bacterial, fungal or yeast origin. In some embodiments, the enzyme is a protease. As used herein, the terms "protease" or "proteinase" refer enzymes that catalyze the hydrolysis of peptide bonds.

As one skilled in the art shall ascertain, enzymes are designed to work with specific types of soils. For example, according to an embodiment of the invention, ware wash applications may use a protease enzyme as it is effective at the high temperatures of the ware wash machines and is effective in reducing protein-based soils. Protease enzymes are particularly advantageous for cleaning soils containing protein, such as blood, cutaneous scales, mucus, grass, food (e.g., egg, milk, spinach, meat residue, tomato sauce), or the like. Protease enzymes are capable of cleaving macromolecular protein links of amino acid residues and convert substrates into small fragments that are readily dissolved or dispersed into the aqueous use solution. Proteases are often referred to as detersive enzymes due to the ability to break soils through the chemical reaction known as hydrolysis. Protease enzymes can be obtained, for example, from *Bacillus subtilis, Bacillus licheniformis* and *Streptomyces griseus*. Protease enzymes are also commercially available as serine endoproteases.

Examples of commercially-available protease enzymes are available under the following trade names: Esperase, Purafect, Purafect L, Purafect Ox, Everlase, Liquanase, Savinase, Prime L, Prosperase and Blap.

The enzyme to be included into the detergent composition may be an independent entity and/or may be formulated in combination with the detergent composition. In some embodiments, the enzyme may be formulated into a detergent composition in either liquid or solid formulations. In addition, enzyme compositions may be formulated into various delayed or controlled release formulations. For example, a solid molded detergent composition may be prepared without the addition of heat. As a skilled artisan will appreciate, enzymes tend to become denatured by the application of heat and therefore use of enzymes within detergent compositions require methods of forming detergent compositions that does not rely upon heat as a step in the formation process, such as solidification.

The enzyme composition may further be obtained commercially in a solid (i.e., puck, powder, etc.) or liquid formulation. Commercially-available enzymes are generally combined with stabilizers, buffers, cofactors and inert vehicles. The actual active enzyme content depends upon the method of manufacture, which is well known to a skilled artisan and such methods of manufacture are not critical to the present invention.

Alternatively, the enzyme composition may be provided separate from the detergent composition, such as added directly to a use solution of a detergent composition or a wash liquor, or wash water of an application, e.g. dishwasher.

Other Additional Detergent Composition Agent

The detergent composition disclosed herein may include one or more additional detergent composition agents. Exemplary additional detergent composition agents include, but are not limited to, a threshold agent; crystal modifier; hardening agent; bleaching agent; peroxycarboxylic acid, peroxycarboxylic acid composition, filler; defoaming agent; anti-redeposition agent; stabilizing agent; dispersant; fragrance and dye; and thickener.

In some embodiments, the detergent composition disclosed herein is free of one, more, or all the additional detergent composition agents.

Anionic Surfactants

Anionic surfactants are surface active substances in which the charge on the hydrophobe is negative; or surfactants in which the hydrophobic section of the molecule carries no charge unless the pH is elevated to neutrality or above (e.g., carboxylic acids). Carboxylate, sulfonate, sulfate and phosphate are the polar (hydrophilic) solubilizing groups found in anionic surfactants. Of the cations (counter ions) associated with these polar groups, sodium, lithium and potassium impart water solubility; ammonium and substituted ammonium ions provide both water and oil solubility; and, calcium, barium, and magnesium promote oil solubility. As those skilled in the art understand, anionic surfactants are excellent detersive surfactants and are therefore favored additions to heavy duty detergent compositions.

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g., alkyl succinates), ether carboxylic acids, sulfonated fatty acids, such as sulfonated oleic acid, and the like. Such carboxylates include alkyl ethoxy carboxylates, alkyl aryl ethoxy carboxylates, alkyl polyethoxy polycarboxylate surfactants and soaps (e.g., alkyl carboxyls). Secondary carboxylates useful in the present compositions include those which contain a carboxyl unit connected to a secondary carbon. The secondary carbon can be in a ring structure, e.g., as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the group-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g., N-acyl sarcosinates), taurates (e.g., N-acyl taurates and fatty acid amides of methyl tauride), and the like.

Suitable anionic surfactants include alkyl or alkylaryl ethoxy carboxylates of the following formula:

R—O—(CH$_2$CH$_2$O)$_n$(CH$_2$)$_m$—CO$_2$X    (3)

in which R is a $C_8$ to $C_{22}$ alkyl group or

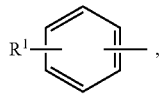

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

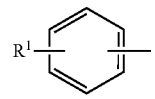

and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12\text{-}13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g., the product Sandopan® DTC, a $C_{13}$ alkyl polyethoxy (7) carboxylic acid.

In some embodiments, the composition or detergent composition disclosed herein is free of an anionic surfactant.

Nonionic Surfactants

Useful nonionic surfactants are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water-soluble compound having the desired degree of balance between hydrophilic and hydrophobic properties. Useful nonionic surfactants include:

Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available from BASF Corp. One class of compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule. Another class of compounds are tetra-functional block copolymers derived from the sequential addition of propylene oxide and ethylene oxide to ethylenediamine. The molecular weight of the propylene oxide hydrotype ranges from about 500 to about 7,000; and, the hydrophile, ethylene oxide, is added to constitute from about 10% by weight to about 80% by weight of the molecule.

Condensation products of one mole of alkyl phenol wherein the alkyl chain, of straight chain or branched chain configuration, or of single or dual alkyl constituent, contains from about 8 to about 18 carbon atoms with from about 3 to about 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples of commercial compounds of this chemistry are available on the market under the trade names Igepal® manufactured by Rhone-Poulenc and Triton® manufactured by Union Carbide.

Condensation products of one mole of a saturated or unsaturated, straight or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade names Lutensol™, Dehydol™ manufactured by BASF, Neodol™ manufactured by Shell Chemical Co. and Alfonic™ manufactured by Vista Chemical Co.

Condensation products of one mole of saturated or unsaturated, straight or branched chain carboxylic acid having from about 8 to about 18 carbon atoms with from about 6 to about 50 moles of ethylene oxide. The acid moiety can consist of mixtures of acids in the above defined carbon atoms range or it can consist of an acid having a specific number of carbon atoms within the range. Examples of commercial compounds of this chemistry are available on the market under the trade names Disponil or Agnique manufactured by BASF and Lipopeg™ manufactured by Lipo Chemicals, Inc.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention for specialized embodiments, particularly indirect food additive applications. All of these ester moieties have one or more reactive hydrogen sites on their molecule which can undergo further acylation or ethylene oxide (alkoxide) addition to control the hydrophilicity of these substances. Care must be exercised when adding these fatty esters or acylated carbohydrates to compositions of the present invention containing amylase and/or lipase enzymes because of potential incompatibility.

Examples of nonionic low foaming surfactants include, but are not limited to, compounds which are modified, essentially reversed, by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from about 1,000 to about 3,100 with the central hydrophile including 10% by weight to about 80% by weight of the final molecule. These reverse Pluronics™ are manufactured by BASF Corporation under the trade name Pluronic™ R surfactants. Likewise, the Tetronic™ R surfactants are produced by BASF Corporation by the sequential addition of ethylene oxide and propylene oxide to ethylenediamine. The hydrophobic portion of the molecule weighs from about 2,100 to about 6,700 with the central hydrophile including 10% by weight to 80% by weight of the final molecule.

Compounds which are modified by "capping" or "end blocking" the terminal hydroxy group or groups (of multifunctional moieties) to reduce foaming by reaction with a small hydrophobic molecule such as propylene oxide, butylene oxide, benzyl chloride; and, short chain fatty acids, alcohols or alkyl halides containing from 1 to about 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.

Additional examples of effective low foaming nonionic surfactants include, but are not limited to the alkylphenoxy-polyethoxyalkanols of U.S. Pat. No. 2,903,486 issued Sep. 8, 1959 to Brown et al. and represented by the formula

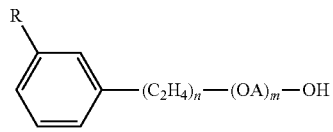

in which R is an alkyl group of 8 to 9 carbon atoms, A is an alkylene chain of 3 to 4 carbon atoms, n is an integer of 7 to 16, and m is an integer of 1 to 10.

The polyalkylene glycol condensates of U.S. Pat. No. 3,048,548 issued Aug. 7, 1962 to Martin et al. having alternated hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.

The defoaming nonionic surfactants disclosed in U.S. Pat. No. 3,382,178 issued May 7, 1968 to Lissant et al. having the general formula $Z[(OR)_nOH]_z$ wherein Z is alkoxylatable material, R is a radical derived from an alkylene oxide which can be ethylene and propylene and n is an integer from, for example, 10 to 2,000 or more and z is an integer determined by the number of reactive oxyalkylatable groups.

The conjugated polyoxyalkylene compounds described in U.S. Pat. No. 2,677,700, issued May 4, 1954 to Jackson et al. corresponding to the formula $Y(C_3H_6O)_n (C_2H_4O)_mH$ wherein Y is the residue of organic compound having from about 1 to 6 carbon atoms and one reactive hydrogen atom, n has an average value of at least about 6.4, as determined by hydroxyl number and m has a value such that the oxyethylene portion constitutes about 10% to about 90% by weight of the molecule.

The conjugated polyoxyalkylene compounds described in U.S. Pat. No. 2,674,619, issued Apr. 6, 1954 to Lundsted et al. having the formula $Y[(C_3H_6O_n(C_2H_4O)_mH]_x$ wherein Y is the residue of an organic compound having from about 2 to 6 carbon atoms and containing x reactive hydrogen atoms in which x has a value of at least about 2, n has a value such that the molecular weight of the polyoxypropylene hydrophobic base is at least about 900 and m has value such that the oxyethylene content of the molecule is from about 10% to about 90% by weight. Compounds falling within the scope of the definition for Y include, for example, propylene glycol, glycerine, pentaerythritol, trimethylolpropane, ethylenediamine and the like. The oxypropylene chains optionally, but advantageously, contain small amounts of ethylene oxide and the oxyethylene chains also optionally, but advantageously, contain small amounts of propylene oxide.

Additional conjugated polyoxyalkylene surface-active agents which are advantageously used in the compositions of this invention correspond to the formula: $P[(C_3H_6O)_n (C_2H_4O)_mH]_x$ wherein P is the residue of an organic compound having from about 8 to 18 carbon atoms and containing x reactive hydrogen atoms in which x has a value of 1 or 2, n has a value such that the molecular weight of the polyoxyethylene portion is at least about 44 and m has a value such that the oxypropylene content of the molecule is from about 10% to about 90% by weight. In either case the oxypropylene chains may contain optionally, but advantageously, small amounts of ethylene oxide and the oxyethylene chains may contain also optionally, but advantageously, small amounts of propylene oxide.

Polyhydroxy fatty acid amide surfactants suitable for use in the present compositions include those having the structural formula $R_2CON_{R1}Z$ in which: R1 is H, $C_1$-$C_4$ hydrocarbyl, 2-hydroxy ethyl, 2-hydroxy propyl, ethoxy, propoxy group, or a mixture thereof; $R_2$ is a $C_5$-$C_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction; such as a glycityl moiety.

The alkyl ethoxylate condensation products of aliphatic alcohols with from about 0 to about 25 moles of ethylene oxide are suitable for use in the present compositions. The alkyl chain of the aliphatic alcohol can either be straight or branched, primary or secondary, and generally contains from 6 to 22 carbon atoms.

The ethoxylated $C_6$-$C_{18}$ fatty alcohols and $C_6$-$C_{18}$ mixed ethoxylated and propoxylated fatty alcohols are suitable surfactants for use in the present compositions, particularly those that are water soluble. Suitable ethoxylated fatty alcohols include the $C_6$-$C_{18}$ ethoxylated fatty alcohols with a degree of ethoxylation of from 3 to 50.

Suitable nonionic alkylpolysaccharide surfactants, particularly for use in the present compositions include those disclosed in U.S. Pat. No. 4,565,647, Llenado, issued Jan. 21, 1986. These surfactants include a hydrophobic group containing from about 6 to about 30 carbon atoms and a polysaccharide, e.g., a polyglycoside, hydrophilic group containing from about 1.3 to about 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside). The inter-saccharide bonds can be, e.g., between the one position of the additional saccharide units and the 2-, 3-, 4-, and/or 6-positions on the preceding saccharide units.

Fatty acid amide surfactants suitable for use the present compositions include those having the formula: $R_6CON(R_7)_2$ in which $R_6$ is an alkyl group containing from 7 to 21 carbon atoms and each $R_7$ is independently hydrogen, $C_1$-$C_4$ alkyl, $C_1$-$C_4$ hydroxyalkyl, or —$(C_2H_4O)_xH$, where x is in the range of from 1 to 3.

A useful class of non-ionic surfactants include the class defined as alkoxylated amines or, most particularly, alcohol alkoxylated/aminated/alkoxylated surfactants. These non-ionic surfactants may be at least in part represented by the general formulae: $R^{20}$—$(PO)_sN$-$(EO)_tH$, $R^{20}$—$(PO)_sN$-$(EO)_tH(EO)_tH$, and $R^{20}$—$N(EO)_tH$; in which $R^{20}$ is an alkyl, alkenyl or other aliphatic group, or an alkyl-aryl group of from 8 to 20, preferably 12 to 14 carbon atoms, EO is oxyethylene, PO is oxypropylene, s is 1 to 20, preferably 2-5, t is 1-10, preferably 2-5, and u is 1-10, preferably 2-5. Other variations on the scope of these compounds may be represented by the alternative formula: $R^{20}$—$(PO)_V$—N[$(EO)_wH$][$(EO)_zH$] in which $R^{20}$ is as defined above, v is 1 to 20 (e.g., 1, 2, 3, or 4 (preferably 2)), and w and z are independently 1-10, preferably 2-5. These compounds are represented commercially by a line of products sold by Huntsman Chemicals as nonionic surfactants. A preferred chemical of this class includes Surfonic™ PEA 25 Amine Alkoxylate. Preferred nonionic surfactants for the compositions of the invention include alcohol alkoxylates, EO/PO block copolymers, alkylphenol alkoxylates, and the like.

The treatise *Nonionic Surfactants*, edited by Schick, M. J., Vol. 1 of the Surfactant Science Series, Marcel Dekker, Inc., New York, 1983 is an excellent reference on the wide variety of nonionic compounds generally employed in the practice of the present invention. A typical listing of nonionic classes, and species of these surfactants, is given in U.S. Pat. No. 3,929,678 issued to Laughlin and Heuring on Dec. 30, 1975. Further examples are given in "Surface Active Agents and detergents" (Vol. I and II by Schwartz, Perry and Berch).

Suitable nonionic surfactants suitable for use with the compositions of the present invention include alkoxylated surfactants. Suitable alkoxylated surfactants include EO/PO copolymers, fully capped or partially EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-$(EO)_5(PO)_4$) and Dehypon LS-36 (R-$(EO)_3(PO)_6$); and capped alcohol alkoxylates, such as Plurafac LF221 and Tegoten EC11; mixtures thereof, or the like.

In some embodiments that are not detergent compositions, the composition disclosed herein is free of a nonionic surfactant.

Semi-Polar Nonionic Surfactants

The semi-polar type of nonionic surfactants are another class of nonionic surfactants useful in compositions disclosed herein. Generally, semi-polar nonionic surfactants are high foaming agents and foam stabilizers, which can limit their application in CIP systems. However, in some embodiments designed for high foaming composition or detergent composition, semi-polar nonionic surfactants would have immediate utility. The semi-polar nonionic surfactants include, but are not limited to, the amine oxides, phosphine oxides, sulfoxides and their alkoxylated derivatives.

Amine oxides are tertiary amine oxides corresponding to the general formula:

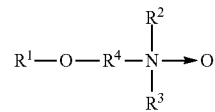

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20.

Useful water soluble amine oxide surfactants are selected from the coconut or tallow alkyl di-(lower alkyl) amine oxides, specific examples of which are dodecyldimethylamine oxide, tridecyldimethylamine oxide, etradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Useful semi-polar nonionic surfactants also include the water-soluble phosphine oxides having the following structure:

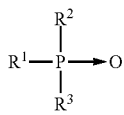

wherein the arrow is a conventional representation of a semi-polar bond; and, $R^1$ is an alkyl, alkenyl or hydroxyalkyl moiety ranging from 10 to about 24 carbon atoms in chain length; and, $R^2$ and $R^3$ are each alkyl moieties separately selected from alkyl or hydroxyalkyl groups containing 1 to 3 carbon atoms.

Examples of useful phosphine oxides include dimethyldecylphosphine oxide, dimethyltetradecylphosphine oxide, methylethyltetradecylphosphone oxide, dimethylhexadecylphosphine oxide, diethyl-2-hydroxyoctyldecylphosphine oxide, bis(2-hydroxyethyl)dodecylphosphine oxide, and bis(hydroxymethyl)tetradecylphosphine oxide.

Semi-polar nonionic surfactants useful herein also include the water soluble sulfoxide compounds which have the structure:

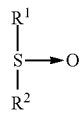

wherein the arrow is a conventional representation of a semi-polar bond; and, $R^1$ is an alkyl or hydroxyalkyl moiety of about 8 to about 28 carbon atoms, from 0 to about 5 ether linkages and from 0 to about 2 hydroxyl substituents; and $R^2$ is an alkyl moiety consisting of alkyl and hydroxyalkyl groups having 1 to 3 carbon atoms.

Useful examples of these sulfoxides include dodecyl methyl sulfoxide; 3-hydroxy tridecyl methyl sulfoxide; 3-methoxy tridecyl methyl sulfoxide; and 3-hydroxy-4-dodecoxybutyl methyl sulfoxide.

Semi-polar nonionic surfactants for the compositions of the invention include dimethyl amine oxides, such as lauryl dimethyl amine oxide, myristyl dimethyl amine oxide, cetyl dimethyl amine oxide, combinations thereof, and the like. Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

In some embodiments, the composition or detergent composition disclosed herein is free of a semi-polar nonionic surfactant.

Cationic Surfactants

Surface active substances are classified as cationic if the charge on the hydrotrope portion of the molecule is positive. Surfactants in which the hydrotrope carries no charge unless the pH is lowered close to neutrality or lower, but which are then cationic (e.g. alkyl amines), are also included in this group. In theory, cationic surfactants may be synthesized from any combination of elements containing an "onium" structure RnX+Y— and could include compounds other than nitrogen (ammonium) such as phosphorus (phosphonium) and sulfur (sulfonium). In practice, the cationic surfactant field is dominated by nitrogen containing compounds, probably because synthetic routes to nitrogenous cationics are simple and straightforward and give high yields of product, which can make them less expensive.

Cationic surfactants preferably include, more preferably refer to, compounds containing at least one long carbon chain hydrophobic group and at least one positively charged nitrogen. The long carbon chain group may be attached directly to the nitrogen atom by simple substitution; or more preferably indirectly by a bridging functional group or groups in so-called interrupted alkylamines and amido amines. Such functional groups can make the molecule more hydrophilic and/or more water dispersible, more easily water solubilized by co-surfactant mixtures, and/or water soluble. For increased water solubility, additional primary, secondary or tertiary amino groups can be introduced, or the amino nitrogen can be quaternized with low molecular weight alkyl groups. Further, the nitrogen can be a part of branched or straight chain moiety of varying degrees of unsaturation or of a saturated or unsaturated heterocyclic ring. In addition, cationic surfactants may contain complex linkages having more than one cationic nitrogen atom.

The surfactant compounds classified as amine oxides, amphoterics and zwitterions are themselves typically cationic in near neutral to acidic pH solutions and can overlap surfactant classifications. Polyoxyethylated cationic surfactants generally behave like nonionic surfactants in alkaline solution and like cationic surfactants in acidic solution.

The simplest cationic amines, amine salts and quaternary ammonium compounds can be schematically drawn thus:

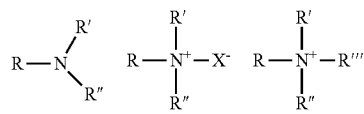

in which, R represents an alkyl chain, R', R", and R'" may be either alkyl chains or aryl groups or hydrogen and X represents an anion. The amine salts and quaternary ammonium compounds are preferred for practical use in this invention due to their high degree of water solubility.

Most large volume commercial cationic surfactants can be subdivided into four major classes and additional sub-groups known to those skilled in the art and described in "Surfactant Encyclopedia", *Cosmetics & Toiletries*, Vol. 104 (2) 86-96

(1989). The first class includes alkylamines and their salts. The second class includes alkyl imidazolines. The third class includes ethoxylated amines. The fourth class includes quaternaries, such as alkylbenzyldimethylammonium salts, alkyl benzene salts, heterocyclic ammonium salts, tetra alkylammonium salts, and the like. Cationic surfactants are known to have a variety of properties that can be beneficial in the present compositions. These desirable properties can include detergency in compositions of or below neutral pH, antimicrobial efficacy, thickening or gelling in cooperation with other agents, and the like.

Cationic surfactants useful in the compositions disclosed herein include those having the formula $R^1{}_m R^2{}_x Y_L Z$ wherein each $R^1$ is an organic group containing a straight or branched alkyl or alkenyl group optionally substituted with up to three phenyl or hydroxy groups and optionally interrupted by up to four of the following structures:

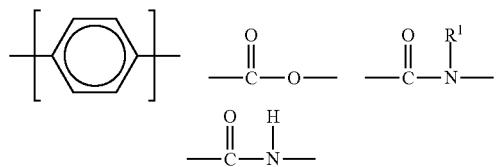

or an isomer or mixture of these structures, and which contains from about 8 to 22 carbon atoms. The $R^1$ groups can additionally contain up to 12 ethoxy groups. m is a number from 1 to 3. Preferably, no more than one $R^1$ group in a molecule has 16 or more carbon atoms when m is 2 or more than 12 carbon atoms when m is 3. Each $R^2$ is an alkyl or hydroxyalkyl group containing from 1 to 4 carbon atoms or a benzyl group with no more than one $R^2$ in a molecule being benzyl, and x is a number from 0 to 11, preferably from 0 to 6. The remainder of any carbon atom positions on the Y group are filled by hydrogens.

Y is can be a group including, but not limited to:

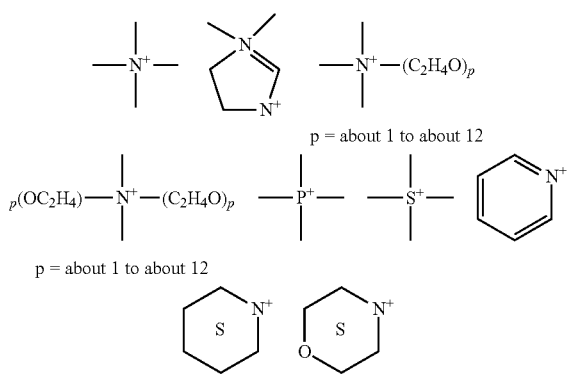

or a mixture thereof. Preferably, L is 1 or 2, with the Y groups being separated by a moiety selected from $R^1$ and $R^2$ analogs (preferably alkylene or alkenylene) having from 1 to about 22 carbon atoms and two free carbon single bonds when L is 2. Z is a water-soluble anion, such as a halide, sulfate, methylsulfate, hydroxide, or nitrate anion, particularly preferred being chloride, bromide, iodide, sulfate or methyl sulfate anions, in a number to give electrical neutrality of the cationic component.

In some embodiments, the composition or detergent composition disclosed herein is free of a cationic surfactant.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" *Cosmetics & Toiletries*, Vol. 104 (2) 69-71 (1989), which is herein incorporated by reference in its entirety. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazole derivatives having application in the present invention generally have the general formula:

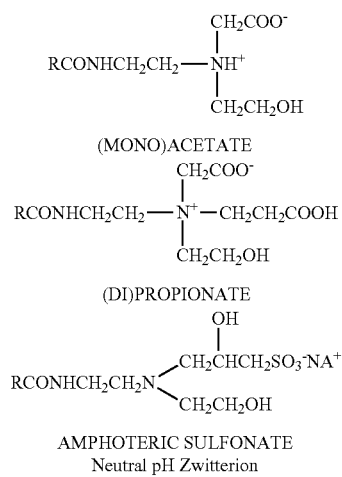

wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which $R=C_8$-$C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—$N^+$($CH_2$—$CH_2$—$CO_2Na)_2$—$CH_2$—$CH_2$—OH or $C_{12}$-alkyl-C(O)—N(H)—$CH_2$—$CH_2$—$N^+$($CH_2$—$CO_2Na)_2$—$CH_2$—$CH_2$—OH. Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch). Each of these references are herein incorporated by reference in their entirety.

In some embodiments, the composition or detergent composition disclosed herein is free of an amphoteric surfactant.

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionic surfactants generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate.

Betaine and sultaine surfactants are exemplary zwitterionic surfactants for use herein. A general formula for these compounds is:

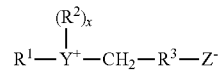

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

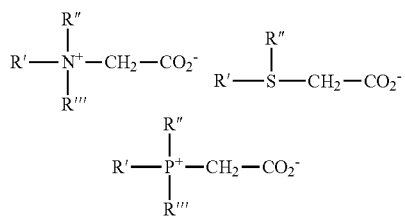

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine;

$C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2N^+R^2SO_3^-$, in which R is a $C_6$-$C_{18}$ hydrocarbyl group, each $R^1$ is typically independently $C_1$-$C_3$ alkyl, e.g., methyl, and $R^2$ is a $C_1$-$C_6$ hydrocarbyl group, e.g., a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch). Each of these references are herein incorporated in their entirety.

In some embodiments, the composition or detergent composition disclosed herein is free of a zwitterionic surfactant.

Gemini Surfactants

While conventional surfactants generally have one hydrophilic group and one hydrophobic group, a Gemini surfactant has at least two hydrophobic groups and at least two hydrophilic groups. These surfactants have the general formula: A1-G-A2 and get their name because they comprise two surfactant moieties (A1, A2) joined by a spacer (G), wherein each surfactant moiety (A1, A2) has a hydrophilic group and a hydrophobic group. Generally; the two surfactant moieties (A1, A2) are the same, but they can be different.

The Gemini surfactants may be anionic; nonionic, cationic or amphoteric. The hydrophilic and hydrophobic groups of each surfactant moiety (A1, A2) may be any of those known to be used in conventional surfactants having one hydrophilic group and one hydrophobic group. For example, a typical nonionic Gemini surfactant, e.g., a bispolyoxyethylene alkyl ether, would contain two polyoxyethylene alkyl ether moieties. Each moiety would contain a hydrophilic group, e.g., polyethylene oxide, and a hydrophobic group, e.g., an alkyl chain.

Anionic and nonionic Gemini surfactants include those of the formula:

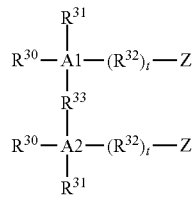

wherein $R^{30}$ is independently $C_1$ to $C_{22}$ alkyl, $R^{34}$—C(O)—, or $R^{34}$—B—$R^{35}$—; wherein $R^{34}$ is $C_1$ to $C_{22}$ alkyl, $R^{35}$ is $C_1$ to $C_{12}$ alkyl, and B is an amide group, —C(O)N($R^{36}$)—, an amino group —N($R^{36}$)—, a carboxyl group —C(O)—O—, a carbonyl group, or a polyether group -(EO)$_a$(PO)$_b$—, wherein EO represents ethyleneoxy radicals, PO represents propyleneoxy radicals, a and b are numbers of from 0 to 100, a is preferably from about 0 to about 30 and b is preferably from about 0 to 10, wherein a plus b is at least one, and the EO and PO radicals can be randomly mixed or in discrete blocks, and $R^{36}$ is hydrogen or $C_1$ to $C_6$ alkyl.

$R^{31}$ is independently hydrogen or $C_1$ to $C_{22}$ alkyl; $R^{32}$ is independently a $C_1$-$C_{10}$ alkyl, —O—, an amide group —C(O)N($R_6$)—, a polyether group —O(EO)$_a$ (PO)$_b$—, —$R^{37}$-D-$R^{37}$—, or -D-$R^{37}$-D-, wherein $R^{37}$ is independently a $C_1$-$C_6$ alkyl and D is —O—, —S—, an amide group —C(O)N($R^{36}$)—, or an amino group —N($R^{36}$)—, wherein $R^{36}$, a and b are as defined above, and t is independently 0 or 1.

Z is independently hydrogen, —SO$_3$Y, —P(O)(OY)$_2$, —COOY, —CH$_2$COOY, —CH$_2$CH(OH)CH$_2$SO$_3$Y and when $R^{32}$ is not a polyether; Z is also —OSO$_3$Y, and —OP(O)(OY)$_2$; wherein Y is hydrogen, alkali metal such as sodium and potassium; alkaline earth metal such as magnesium and calcium; ammonium; or organic base salt such as monoethanolamine, diethanolamine, triethanolamine, triethylamine, trimethylamine, N-hydroxyethyl morpholine, and the like.

A1 or A2 is independently a straight chain or branched $C_1$ to $C_6$ alkyl, an O—$R_5$—O— group or aryl; preferably phenyl; $R^{33}$ is a bond, an aryl group such as a phenyl or diphenyl group, a $C_1$ to $C_{10}$ alkyl group, preferably a $C_1$ to $C_4$ alkyl group, most preferably methylene, —C≡C—, —O—, —S—, —S—S—, —N($R^{36}$)—, —$R^{35}$O—, —$R^{35}$O(EO)$_a$(PO)$_b$—, -D$_1$-$R^{38}$-D$_1$- or —$R^{38}$-D$_1$-$R^{38}$—, wherein $R^{38}$ is independently a $C_1$-$C_{10}$ alkyl group, —C(O)—, —$R^{35}$O(EO)$_a$(PO)$_b$—, —O—$R^{35}$—O—, or aryl, e.g. phenyl, and D$_1$ is independently —O—, —S—, —S—S—, —SO$_2$—, —C(O)—, a polyether group —O(EO)$_a$(PO)$_b$—, an amide group —C(O)N($R^{36}$)—, an amino group —N($R^{36}$)—, —O—$R_5$—O—, or aryl wherein $R^{35}$, $R^{36}$, a and b are as defined above.

On the formulae of this disclosure, the term "alkali" includes substituted alkali, especially the hydroxy substituted derivatives thereof and straight as well as branched chains. When Z is hydrogen, the gemini surfactants are nonionic.

Other Gemini surfactants specifically useful in the present disclosure include gemini anionic or nonionic surfactants of the formulae:

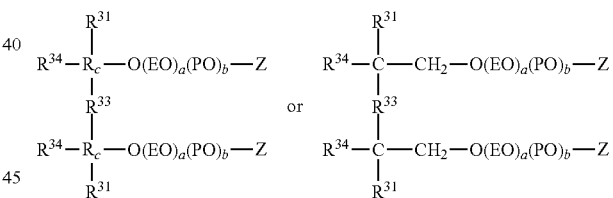

wherein $R_c$ represents aryl, preferably phenyl. $R^{31}$, $R^{33}$, $R^{34}$, and Z are as defined above. a and b are numbers of from 0 to 100, a is preferably from about 0 to about 30 and b is preferably from about 0 to 10, wherein a plus b is at least one, and the EO and PO radicals can be randomly mixed or in discrete blocks.

The primary hydroxyl group of these surfactants can be readily phosphated, sulfated or carboxylated by standard techniques.

In some embodiments, the composition or detergent composition disclosed herein is free of a Gemini surfactant.

As used herein, the term "substantially free", "free" or "free of" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

The term "weight percent", "wt-%", "percent by weight", "% by weight", and variations thereof, as used herein, refer to the concentration of a substance as the weight of that substance divided by the total weight of the composition and multiplied by 100. It is understood that, as used here, "percent", "%", and the like are intended to be synonymous with "weight percent", "wt-%", etc.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

General Scheme to Synthesize Exemplary Di-Cationic Compounds Containing Two Quaternary Groups:

Exemplary di-cationic compounds containing two quaternary groups as disclosed herein were synthesized, by aza Michael addition reaction between a primary amine (1 mole) and α,β-unsaturated carbonyl compound, an activated olefin, containing at least one quaternary group (at least 2 moles). The generic synthesis reaction scheme for preparation of disclosed di-cationic compounds is shown in FIG. 2.

In FIG. 2, $R^{11}$ is $R^1$ or $R^1$—Z—$(CH_2)_m$—; $R^1$ is an unsubstituted or substituted, linear or branched $C_1$-$C_{30}$ alkyl, cyclic alkyl, alkenyl, or alkynyl group; Z is NH or O; $R^2$ is H, $CH_3$, or an unsubstituted, linear or branched $C_2$-$C_{10}$ alkyl, alkenyl, or alkynyl group; m is an integer of 1 to 4; and n is an integer of 1-20.

The reaction shown in FIG. 2 can be carried out in water at 80° C. The progression of this reaction is monitored by ESI-MS and/or NMR spectroscopy for consumption of the monomer. The reaction is typically stopped at time when a yield of about 98% for the diquat product is obtained. The synthesized compounds in the following Examples were made according to this scheme, except the reactants were different in each of the Examples as set forth in further detailed in each Example.

Example 2

Synthesis of 3,3'-((3,3'-(octylazanediyl)bis(propanoyl)bis(azanediyl))bis(N,N,N-trimethylpropan-1-aminium) Chloride (I)

In this Example, (3-acrylamidopropyl) trimethylammonium chloride (APTAC, 75%, 30 grams, 0.10 mol) was charged into a 250-mL three-necked round bottom flask (RBF) equipped with an overhead stirrer, temperature probe, and condenser. Benzyltrimethylammonium hydroxide (0.9 grams, 10%, 0.0005 mol) and water (41 g) were added into the flask. Octylamine (7 grams, 99%, 0.053 mol) was then added portion wise to the well-stirred reaction mixture. The resulting suspension was stirred at 80° C. overnight. As the reaction proceeded to completion, the suspension turned into a clear yellowish solution. The resulting (~37 wt %) aqueous solution of the diquat compound, 3,3'-((3,3'-(octylazanediyl)bis(propanoyl))bis(azanediyl))bis(N,N,N-trimethylpropan-1-aminium) chloride (referred as compound I), was stored in the container. Mass spectrometry (+ESI-MS) confirmed synthesis of the di-cationic compound I: calc. $[M-2Cl^-]^{2+}$ 235.73, found 235.7241; calc. $[M-Cl^-]^+$ 506.42, found 506.4182.

Example 3

Synthesis of 3,3'-((3,3'-(dodecylazanediyl)bis(propanoyl)bis(azanediyl))bis(N,N,N-trimethylpropan-1-aminium) Chloride (II)

In this Example, (3-acrylamidopropyl) trimethylammonium chloride (APTAC, 75%, 30 grams, 0.10 mol) was charged into a 250-mL three-necked RBF equipped with an overhead stirrer, temperature probe, and condenser. Benzyltrimethylammonium hydroxide (0.9 grams, 10%, 0.0005 mol) and water (63 g) were added into the flask. Dodecylamine (10 grams, 98%, 0.053 mol) was then added portion wise to the well-stirred reaction mixture. The resulting suspension was stirred at 80° C. overnight. As the reaction proceeded to completion, the suspension turned into a clear yellowish solution. The resulting (~31 wt %) aqueous solution of the diquat compound, 3,3'-((3,3'-(dodecylazanediyO-bis(propanoyl))bis(azanediyl))bis(N,N,N-trimethylpropan-1-aminium) chloride (referred as compound II) was used as is. Mass spectrometry (+ESI-MS) confirmed synthesis of the diquat compound (II): calc. $[M-2Cl^-]^{2+}$ 263.76, found 263.7554; calc. $[M-Cl^-]^+$ 562.48, found 562.4806.

Example 4

Synthesis of 3,3'-((3,3'-(hexadecylazanediyl)bis(propanoyl)bis(azanediyl))bis(N,N,N-trimethylpropan-1-aminium) Chloride (III)

In this Example, (3-acrylamidopropyl) trimethylammonium chloride (APTAC, 75%, 41 grams, 0.149 mol) was charged into a 250-mL three-necked RBF equipped with an overhead stirrer, temperature probe, and condenser. Benzyltrimethylammonium hydroxide (0.9 grams, 10%, 0.0005 mol) and water (100 g) were added into the flask. Hexadecylamine (20 grams, 90%, 0.0745 mol) was then added portion wise to the well-stirred reaction mixture. The resulting suspension was stirred at 80° C. overnight. As the reaction proceeded to completion, the suspension turned into a clear yellowish solution. The resulting (~30 wt %) aqueous solution of the diquat compound, 3,3'-((3,3'-(hexadecylazanediyObis(propanoyl))bis(azanediyl))bis(N,N,N-trimethylpropan-1-aminium) chloride (referred as compound III), was used as is. Mass spectrometry (+ESI/MS) confirmed synthesis of the diquat compound (III): calc. $[M-2Cl^-]^{2+}$ 291.79, found 291.7870; calc. $[M-Cl^-]^+$ 618.54, found 618.5439.

Example 5

Synthesis of 3,3'-((3,3'-(octylazanediyl)bis(propanoyl)bis(azanediyl))bis(N,N,N-trimethylpropan-1-aminium) Chloride (IV)

In this Example, (3-acrylamidopropyl) trimethylammonium chloride (APTAC, 75%, 40 grams, 0.145 mol) was charged into a 250-mL three-necked RBF equipped with an overhead stirrer, temperature probe, and condenser. Benzyltrimethylammonium hydroxide (0.9 grams, 10%, 0.0005 mol) and water (100 g) were added into the flask. Octadecylamine (20 grams, 98%, 0.072 mol) was then added portion wise to the well-stirred reaction mixture. The resulting suspension was stirred at 80° C. overnight. As the reaction proceeded to completion, the suspension turned into a clear yellowish solution. The resulting (~31 wt %) aqueous solution of the diquat compound, 3,3'-((3,3'-(octylazanediyObis(propanoyl))bis(azanediyl))bis(N,N,N-trimethylpropan-1-aminium) chloride (referred as compound IV), was used as is. Mass spectrometry (+ESI-MS) confirmed synthesis of the diquat compound IV: calc. [M-2Cl⁻]²⁺ 305.80, found 305.8014; calc. [M-Cl⁻]⁺ 646.58, found 648.5791.

Example 6

Synthesis of 3,3'-((3,3'-(octadec-9-en-1-ylazanediyl)) bis(propanoyl)) bis(azanediyl)) bis(N,N,N-trimethylpropan-1-aminium) Chloride (V)

In this Example, (3-acrylamidopropyl) trimethylammonium chloride (APTAC, 75%, 30 grams, 0.109 mol) was charged into a 250-mL three-necked RBF equipped with an overhead stirrer, temperature probe, and condenser. Benzyltrimethylammonium hydroxide (0.25 grams, 10%, 0.0001 mol) and water (70 g) were added into the flask. Oleylamine (15 grams, 95%, 0.053 mol) was then added portion wise to the well-stirred reaction mixture. The resulting suspension was stirred at 80° C. overnight. As the reaction proceeded to completion, the suspension turned into a clear yellowish solution. The resulting (~32 wt %) aqueous solution of the diquat compound, 3,3'-((3,3'-(octadec-9-en-1-ylazanediyl) bis(propanoyl)) bis(azanediyl)) bis(N,N,N-trimethylpropan-1-aminium) chloride (referred as V), was used as is. Mass spectrometry (+ESI-MS) confirmed synthesis of the diquat compound: calc. [M-2Cl⁻]²⁺ 304.80, found 304.7949; calc. [M-Cl⁻]⁺ 644.56, found 644.5596.

Example 7

Synthesis of 3,3'-((3,3'-((3-(octadec-9-en-1-ylamino) propyl)azanediyl)bis(propanoyl))bis (Azanediyl)) bis(N,N,N-trimethylpropan-1-aminium) Chloride (VI)

In this Example, (3-acrylamidopropyl) trimethylammonium chloride (APTAC, 75%, 42 grams, 0.152 mol) was charged into a 250-mL three-necked RBF equipped with an overhead stirrer, temperature probe, and condenser. Benzyltrimethylammonium hydroxide (0.25 grams, 10%, 0.0001 mol) and water (130 g) were added into the flask. N-oleylpropanediamine (25 grams, 99%, 0.076 mol) was then added portion wise to the well-stirred reaction mixture. The resulting suspension was stirred at 80° C. overnight. As the reaction proceeded to completion, the suspension turned into a clear yellowish solution. The resulting (~28 wt %) aqueous solution of the diquat compound, 3,3'-((3,3'-((3-(octadec-9-en-1-ylamino)propyl)azanediyl)bis(propanoyl))bis (azanediyl)) bis(N,N,N-trimethylpropan-1-aminium) chloride (referred as VI), was used as is. Mass spectrometry (+ESI/MS) confirmed synthesis of the diquat compound VI: calc. [M-2Cl⁻]²⁺ 333.32, found 333.3238; calc. [M-Cl⁻]⁺ 701.62, found 701.6173.

Example 8

Surface Tension Measurements

Surface tension measurements were conducted on a Tracker tensiometer (Teclis Instruments) at room temperature. Various solutions with different concentrations of the exemplary di-cationic compounds were prepared, and surface tension measurements were conducted. The surface tension as a function of concentration of the exemplary di-cationic compounds were measured and are listed in Table 1.

TABLE 1

Surface tension measurements of the exemplary diquat compounds (I-VI)

| Concentration (%) | Surface Tension (dynes/cm) | | | | | |
|---|---|---|---|---|---|---|
| | I | II | III | IV | V | VI |
| 0.010 | 49.19 | 53.35 | 70.43 | 68.98 | 69.3 | 61.78 |
| 0.025 | 44.36 | 46.29 | 53.79 | 53.29 | 54.24 | 57.85 |
| 0.050 | 35.86 | 43.64 | 48.49 | 50.25 | 43.95 | 46.67 |
| 0.100 | 31.85 | 42.20 | 46.07 | 50.57 | 39.81 | 45.32 |
| 0.500 | 25.1 | 36.36 | 45.61 | 47.13 | 40.84 | 44.81 |

The inventions being thus described, it will be obvious that the same may be varied in many ways. Such variations are not to be regarded as a departure from the spirit and scope of the disclosures and all such modifications are intended to be included within the scope of the following claims.

The above specification provides a description of the novel compounds, their synthesis and use, and the compositions, products, or articles that comprise the disclosed compounds. Since many embodiments can be made without departing from the spirit and scope of the disclosure, the invention resides in the claims.

What is claimed is:

1. A method to synthesize a compound, comprising: contacting a primary amine with an activated olefin having a hydrophilic group to
generate a compound;
wherein the primary amine is $R^{11}$—$NH_2$, wherein $R^{11}$ is $R^1$—Z—$(CH_2)_m$—; and
wherein the activated olefin is X is O;

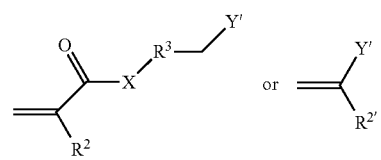

$R^1$ is an unsubstituted or substituted linear or branched $C_1$-$C_{30}$ alkyl, cyclic alkyl, alkenyl, or alkynyl group;
Z is O;
$R^2$ is H, $CH_3$, or an unsubstituted linear or branched $C_1$-$C_{10}$ alkyl, alkenyl, or alkynyl group;
$R^{2'}$ is H, $CH_3$, or an unsubstituted or substituted linear or branched $C_1$-$C_{10}$ alkyl, alkenyl, alkynyl group,—COOH, —$CH_2$COOH, Y', or —$(CH_2)_m$—Y';
m is an integer of 1 to 4;
$R^3$ is absent or an unsubstituted linear $C_1$- or $C_5$-$C_{30}$ alkylene group; and
Y' is —COOH,—$PO_3H$,—$SO_3H$,—$OSO_3H$,-$OPO_3H$, or a salt thereof.

2. The method of claim 1, wherein the contacting step is done in the presence of a reaction solvent, of a reaction solvent and alkalinity source, of a reaction solvent and acid, or of a reaction solvent and a catalyst.

3. The method of claim 2, wherein the reaction solvent is water, methanol, ethanol, propanol, glycol, PEG, or a mixture thereof.

4. The method of claim 1, wherein the contacting step is done in the presence of benzyltrimethylammonium hydroxide.

5. The method of claim 1, wherein the activated olefin is

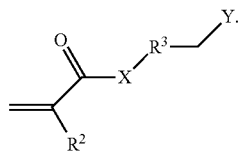

6. The method of claim 1, wherein the activated olefin is

7. An article, product, or composition comprising one or more compounds according to Formulas II or III:

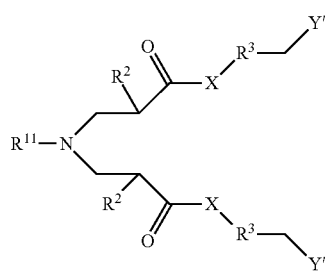

wherein:
X is O;
$R^{11}$ is $R^1$—Z—$(CH_2)_m$—;
$R^1$ is an unsubstituted or substituted linear or branched $C_1$-$C_{30}$ alkyl, cyclic alkyl, alkenyl, or alkynyl group;
Z is O;
$R^2$ is H, $CH_3$, or an unsubstituted linear or branched $C_1$-$C_{10}$ alkyl, alkenyl, or alkynyl group;
$R^{2'}$ is H, $CH_3$, or an unsubstituted or substituted linear or branched $C_1$-$C_{10}$ alkyl, alkenyl, alkynyl group,—COOH,—$CH_2$COOH, Y', or —$(CH_2)_m$—Y';
m is an integer of 1 to 4;
$R^3$ is absent or an unsubstituted linear $C_1$ or $C_5$-$C_{30}$ alkylene group; and
Y' is —COOH, —$PO_3H$, —$SO_3H$, —$OSO_3H$, —$OPO_3H$, or a salt thereof.

8. The article, product, or composition of claim 7, wherein the article, product or composition further comprises a carrier solvent and is an aqueous article, product, or composition.

9. The article, product, or composition of claim 8, wherein the carrier solvent is water, an alcohol, an alkylene glycol, an alkylene glycol alkyl ether, or a combination thereof.

10. The article, product, or composition of claim 7, wherein the article, product, or composition further comprises a primary alkalinity source and is a detergent composition.

11. The article, product, or composition of claim 10, wherein the article, product, or composition further comprises a chelant.

12. The article, product, or composition of claim 10, wherein the article, product, or composition further comprises an enzyme.

13. The article, product, or composition of claim 10, wherein the article, product, or composition further comprises an additional detergent composition agent.

14. The article, product, or composition of claim 7, further comprising an additional surfactant, wherein the additional surfactant is a nonionic, semi-nonionic, cationic, anionic, amphoteric, zwitterionic, Gemini, surfactant or mixtures thereof.

15. The article, product, or composition of claim 7, wherein one or more compounds is Formula II

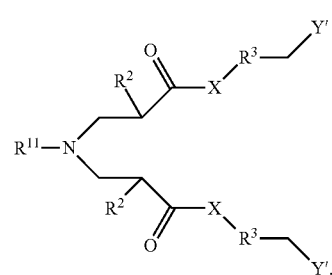

16. The article, product, or composition of claim 7, wherein one or more compounds is Formula III

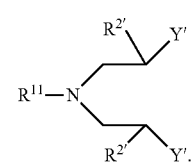

17. A compound according to Formulas II or III

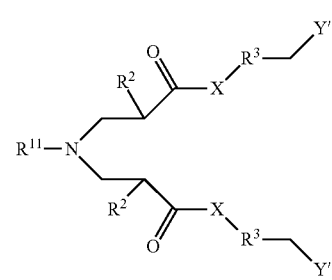

-continued

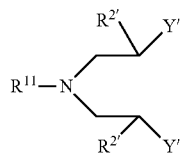
(III)

wherein:

X is O;

$R^{11}$ is $R^1$—Z—$(CH_2)_m$—;

$R^1$ is an unsubstituted or substituted linear or branched $C_1$-$C_{30}$ alkyl, cyclic alkyl, alkenyl, or alkynyl group;

Z is O;

$R^2$ is H, $CH_3$, or an unsubstituted linear or branched $C_1$-$C_{10}$ alkyl, alkenyl, or alkynyl group;

$R^{2'}$ is H, $CH_3$, or an unsubstituted or substituted linear or branched $C_1$-$C_{10}$ alkyl, alkenyl, alkynyl group, —COOH, —CH2COOH, Y', or —$(CH_2)_m$—Y';

m is an integer of 1 to 4;

$R^3$ is absent or an unsubstituted linear $C_1$ or $C_5$-$C_{30}$ alkylene group; and Y' is —COOH, —$PO_3H$, —$SO_3H$, —$OSO_3H$, —$OPO_3H$, or a salt thereof.

18. The compound of claim 17, wherein the compound is Formula II

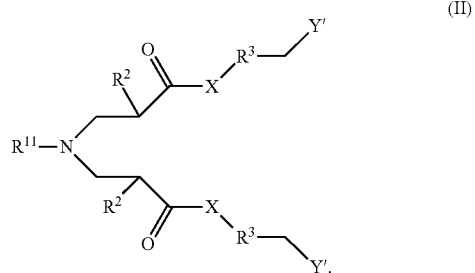
(II)

19. The compound of claim 17, wherein the compound is Formula III

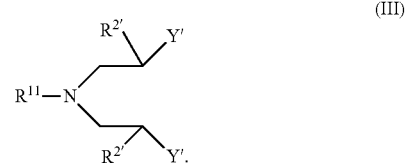
(III)

20. The compound of claim 17, wherein the compound further comprises a carrier solvent, which comprises water, an alcohol, an alkylene glycol, an alkylene glycol alkyl ether, or a combination thereof.

* * * * *

UNITED STATES PATENT AND TRADEMARK OFFICE
CERTIFICATE OF CORRECTION

| | | |
|---|---|---|
| PATENT NO. | : 12,103,881 B2 | Page 1 of 1 |
| APPLICATION NO. | : 17/648442 | |
| DATED | : October 1, 2024 | |
| INVENTOR(S) | : Ashish Dhawan and Carter M. Silvernail | |

It is certified that error appears in the above-identified patent and that said Letters Patent is hereby corrected as shown below:

In the Claims

In Claim 5, Column 41, at approximately Lines 13-20:

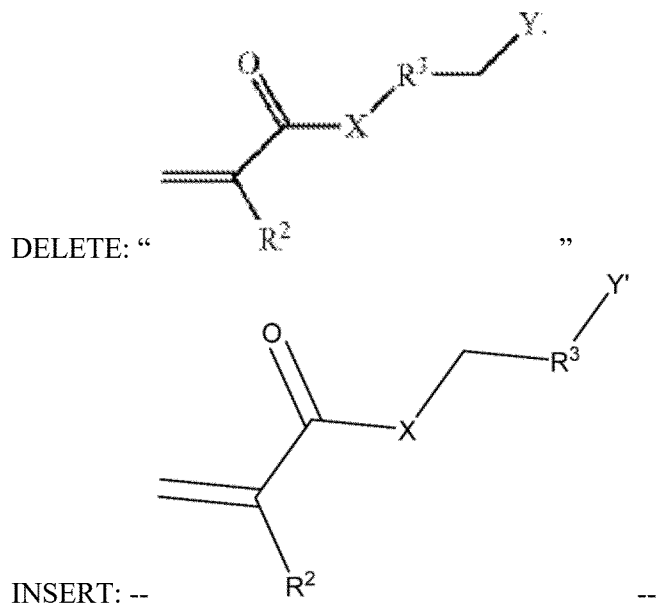

In Claim 17, Column 43, at approximately Line 23:
DELETE: "-CH2COOH,"
INSERT: -- -CH$_2$COOH,--

Signed and Sealed this
Eighteenth Day of March, 2025

Coke Morgan Stewart
*Acting Director of the United States Patent and Trademark Office*